US008741955B2

(12) United States Patent
Foster et al.

(10) Patent No.: US 8,741,955 B2
(45) Date of Patent: Jun. 3, 2014

(54) D-SERINE TRANSPORTER INHIBITORS AS PHARMACEUTICAL COMPOSITIONS FOR THE TREATMENT OF CENTRAL NERVOUS SYSTEM DISORDERS

(75) Inventors: Alan C. Foster, San Diego, CA (US); Yong-Xin Li, Mission Viejo, CA (US); Ursula Staubli, Laguna Beach, CA (US); Veena Viswanath, Irvine, CA (US); Lauren Luhrs, Rancho Santa Margarita, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/480,221

(22) Filed: May 24, 2012

(65) Prior Publication Data
US 2012/0329851 A1 Dec. 27, 2012

Related U.S. Application Data

(60) Provisional application No. 61/490,652, filed on May 27, 2011.

(51) Int. Cl.
*A01N 37/12* (2006.01)
*A01N 37/44* (2006.01)
*A61K 31/195* (2006.01)

(52) U.S. Cl.
USPC .......................................... 514/563; 514/567

(58) Field of Classification Search
USPC ................................................. 514/563, 567
See application file for complete search history.

(56) References Cited

U.S. PATENT DOCUMENTS

| 4,166,452 | A | | 9/1979 | Generales, Jr. | |
|---|---|---|---|---|---|
| 4,256,108 | A | | 3/1981 | Theeuwes | |
| 4,265,874 | A | | 5/1981 | Bonsen et al. | |
| 5,602,150 | A | * | 2/1997 | Lidsky | 514/327 |
| 2002/0010212 | A1 | | 1/2002 | Javitt | |
| 2002/0183390 | A1 | * | 12/2002 | Javitt | 514/561 |
| 2005/0159488 | A1 | | 7/2005 | Javitt | |

FOREIGN PATENT DOCUMENTS

| WO | 03-077998 | | 9/2003 |
|---|---|---|---|
| WO | WO 2011/053636 | * | 5/2011 |

OTHER PUBLICATIONS

Schizophrenia, National Institutes of Mental Health, 2013.*
Alzheimer Disease Fact Sheet, National Institutes of Aging, 2013.*
Broer et al., "The Astroglial ASCT2 Amino Acid Transporter as a Mediator of Glutamine Efflux"; J. Neurochem., vol. 73, No. 5, pp. 2184-2194, 1999.
Citri, et al. "Synaptic Plasticity: Multiple Forms, Functions, andMechanisms", Neuropsychopharmacology Reviews 33, 18-41, (2008).
Cooke and Bear, "Visual Experience Induces Long-Term Potentiation in the Primary Visual Cortex"; The Journal of Neuroscience, 30(48):16304-16313, Dec. 1, 2010.
Coyle, "Glutamate and Schizophrenia: Beyond the Dopamine Hypothesis", Cellular and Molecular Neurobiology, vol. 26, Nos. 4-6, Jul./Aug. 2006.
Esslinger, "Nc-Aryl glutamine analogues as probes of the ASCT2 Neutral Amino Acid Transporter Binding Site", Bioorganic Med Chern 13:1111-1118, (2005).
Field et al, "Targeting glutamate synapses in schizophrenia", Trends in Molecular Medicine, vol. 17, No. 12, Dec. 2011.
Fossat et al, "Glial D-Serine Gates NMDA Receptors at Excitatory Synapses in Prefrontal Cortex" Cerebral Cortex;22:595-606, Mar. 2012.
Foster , et al. "Glutamate- and GABA-Based CNS Therapeutics", Curr Opin Pharmacol; 6 : 7-17, (2006).
Grewer C and Grabsch E "New Inhibitors for the Neutral Amino Acid Transporter ASCT2 Reveal its Na+ -Dependent Anion Leak", J Physiol557.3:747-759, (2004).
Harveit et al., "Neurotransmitter Receptors Mediating Excitatory Input to Cells in the Cat Lateral Geniculate Nucleus. II Nonlagged Cells", Journal of Neurophysiology, vol. 63, No. 6, Jun. 1990.
Henneberger , et al. "Long Term Potentiation Depends on Release of D-Serine From Astrocytes", Nature. 463(7278): 232-236. doi:10.1038/nature08673, 2010.
Johnson, et al. "Glycine Potentiates the NMDA Response in Culture Mouse Brain Neurons", Nature vol. 325, pp. 529-531, 1987.
Labrie, et al.; "The involvement of the NMDA receptor D-serine/glycine site in the pathophysiology and treatment of schizophrenia"; Neuroscience and Biobehavioral Reviews 34, 351-372; (2010).
Lynch et al, "The likelihood of cognitive enhancement", Pharmacology, Biochemistry and Behavior 99 116-129, (2011).
Mothet , et al. "D-Serine is an Endogenous Ligand for the Glycine Site of the N-methyl-D-Aspartate Receptor" Proc Natl Acad Sci 97:4926-4931, (2000).
Paoletti and Neyton, "NMDA Receptor Subunits: Function and Pharmacology", Current Opinion in Pharmacology, 7:39-47, 2007.
Pinilla-Tenas et al., "Transport of Proline and Hydroxyproline by the Neutral Amino-Acid Exchanger ASCT1", J. Membrane Biol. 195, 27-32 (2003).
Regan, "Rapid objective refraction using evoked brain potentials"; Investigative Ophthalmology; 12, 669-679, 1973.
Reminton's Pharmaceutical Sciences, Mack Publishing Company, Easton, Pa., 16th Edition, 1980.

(Continued)

*Primary Examiner* — Sreeni Padmanabhan
*Assistant Examiner* — Uma Ramachandran
(74) *Attorney, Agent, or Firm* — Doina G. Ene

(57) ABSTRACT

The present invention relates to pharmaceutical compositions comprising D-serine transporter inhibitors and therapeutic methods using such pharmaceutical compositions in methods for the treatment of central nervous system disorders.

3 Claims, 18 Drawing Sheets

(56) References Cited

OTHER PUBLICATIONS

Ribeiro et al., "Glial Transport of the neuromodulator D-Serine", Brain Research 929, 202-209, (2002).
Rosenberg, et al., "Neuronal release of D-serine: a physiological Pathway Controlling Extracellular D-Serine Concentration", FASEB Journal article fj.09-147967. Published online Apr. 6, 2010.
Rutter et al., "Evidence From Gene Knockout Studies Implicates Asc-1 as the Primary Transporter Mediating D-Serine Reuptake in the Mouse CNS", European Journal of Neuroscience, vol. 25, pp. 1757-1766, 2007.
Scharfman, et al. "N-Methyl-D-Aspartate Receptors Contribute to Excitatory Postsynaptic Potentials of Cat Lateral Geniculate Neurons Recorded in Thalamic Slices"; Proc. Natl. Acad. Sci. USA, vol. 87, pp. 4548-4552, Jun. 1990.
Shafqat et al., "Cloning and Expression of a Novel Na+-dependent Neutral Amino Acid Transporter Structurally Related to Mammalian Na+/Glutamate Cotransporters*", Journal of Biological Chemestry, vol. 268, No. 21, pp. 15351-15355, 1993.
Stevens et al., "D-Serine and Serine Racemase Are Present in the Vertebrate Retina and Contribute to the Physiological Activation of NMDA receptors", PNAS, vol. 100, No. 11, pp. 6789-6794, 2003.
Swerdlow and Geyer, "Using an Animal Model of Deficient Sensorimotor Gating to Study the Pathophysiology and New Treatments of Schizophrenia", Schizophrenia Bulletin, vol. 24, No. 2, 1998.
Torres-Zamorano et al., "Sodium-Dependent Homo- and Hetero-Exchange of Neutral Amino Acids Mediated by the Amino Acid Transporter ATB", Biochemical and Biophysical Research Communications 245, 824-829 (1998).
Traynelis et al, "Glutamate Receptor Ion Channels: Structure, Regulation, and Function",Pharmacological Reviews, vol. 62, No. 3, 2010.
Utsunomiya-Tate et al., "Cloning and Functional Characterization of a System ASC-like Na1-dependent Neutral Amino Acid Transporter*", The Journal of Biological Chemistry, vol. 271, No. 25, Issue of Jun. 21, pp. 14883-14890, 1996.
Xie et al., << Lack of the Alanine—Serine—Cysteine Transporter 1 Causes Tremors, Seizures, and Early Postnatal Death in Mice, Brain Research 1052, pp. 212-221, (2005).
Yamamoto et al., Functional Identification of ASCT1 Neutral Amino Acid Transporter As the Predominant System for the Uptake of L-Serine in Rat Neurons in Primary Culture, Neuroscience Research 49, pp. 101-111, (2004).
Yang et al., "Contribution of Astrocytes to Hippocampal Long-Term Potentiation Through Release of D-Serine", PNAS, vol. 100, No. 25, pp. 15194-15199, 2003.
Dun, Y. et al, 2007, Functional and Molecular Analysis of D-Serine Transport in Retinal Muller Cells, Experimental Eye Research, 84, 191-199.
Lynch, James et al, 2006, (L)-Phenylglycine, But Not Necessarily Other alpha2delta Subunit Voltage-Gated Calcium Channel Ligands, Attenuates Neuropathic Pain in Rats, Pain, 125, 136-142.
O'Brien, Kylie et al, 2005, D-Serine Uptake by Isolated Retinas is Consistent with ASCT-Mediated Transport, Neuroscience Letters, 385, 58-63.
Shao, Zongjun et al, 2009, Functional and Immunocytochemical Characterization of D-Serine Transporters in Cortical Neuron and Astrocyte Cultures, Journal of Neuroscience Research, 87, 2520-2530.
Thomsen, C. et al, 2001, Characterisation of D-Serine Transporter and Functional Modulation of NMDA Receptors, Abstract of the Annual Meeting of the Society for Neuroscience, 27, 917.3.
Thomsen, Christian et al, 1994, (S)-4-Carboxy-3-Hydroxyphenylglycine, an Antagonist of Metabotropic Glutamate Receptor (mGluR)1a and an Agonist of mGluR2, Protects Against Audiogenic Seizures in DBA/2 Mice, Journal of Neurochemistry, 62, 2492-2495.
Patent Cooperation Treaty, Notification of Transmittal of the International Search Report and the Written Opinion of the International Searching Authority, or the Declaration, Form PCT/ISA/220, Int. App. No. PCT/US2012/039428, Aug. 1, 2012.
Smith et al, The Behavioral and Neurochemical Effects of a Novel D-Amino Acid Oxidase Inhibitor Compound 8 [4H-Thieno [3,2-b]pyrrole-5-carboxylic Acid] and D-Serine, The Journal of Pharmacology and Experimental Therapeutics, 2009, 921-930, 328.
Thomas E. Krahe and Alexandre E. Medina, Activation of NMDA Receptors Is Necessary for the Recovery of Cortical Binocularity, Mar. 16, 2010, Journal of Neurophysiology 103: 2700-2706, 103.

* cited by examiner

Figure 1

| Compound | IC$_{50}$ in Astrocytes (µM) | IC$_{50}$ in Synaptosomes (µM) |
|---|---|---|
| L-serine | 57.9 | 9.6 |
| D-serine | 1581 | 9.4 |
| L-glutamine | 1641 | 943 |
| L-asparagine | 57.2 | 668 |
| L-GPNA | 3096 | 453 |
| L-glutamate-γ-benzyl ester | 3000 | 62 |
| L-4-fluorophenylglycine | 27.9 | 258 |
| L-4-hydroxyphenylglycine | 142.1 | 101 |
| DL-2-fluorophenylglycine | 1571 | 348 |
| L-phenylglycine | 89.4 | 217 |
| L-proline | 2271 | >10,000 |
| L-trans-4-hydroxyproline | 38.9 | >10,000 |
| S-benzyl-L-cysteine | 424 | 86 |
| S-phenyl-L-cysteine | 597 | 29.3 |

L-GPNA: L-γ-nitrophenyl glutamyl anilide.

Figure 1B: Dose-response for L-4OHPG enhancement of NMDA Receptor-Mediated Excitatory Postsynaptic Currents (EPSC)
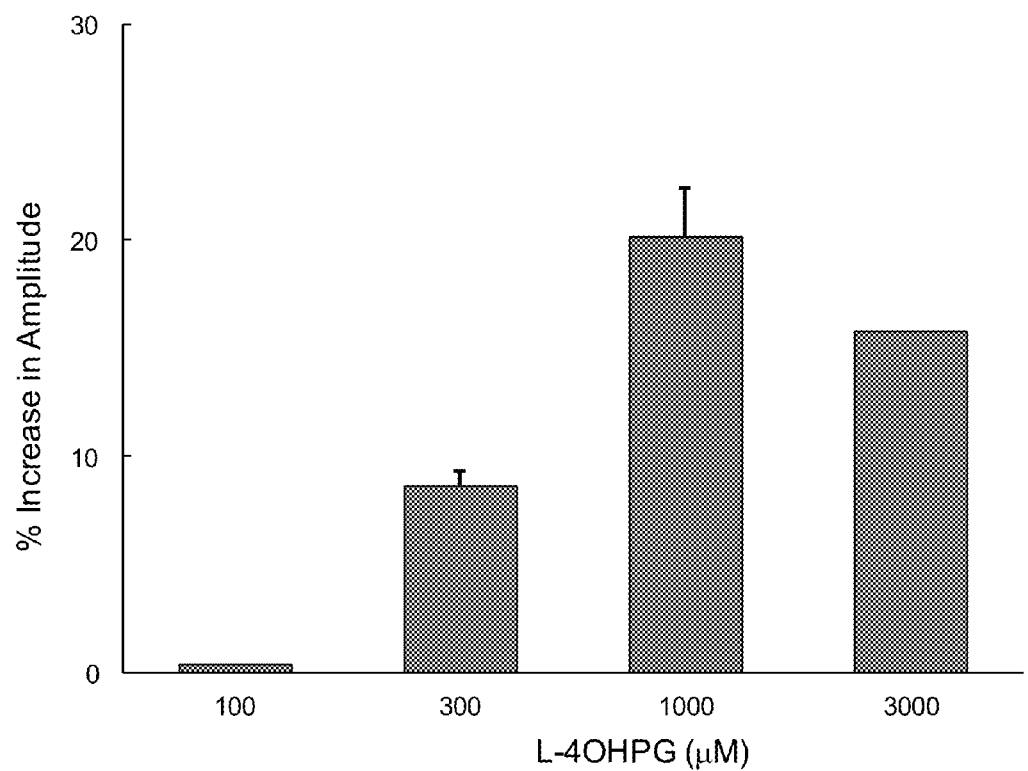

Figure 2

| Compound | IC$_{50}$ Astrocytes (µM) | IC$_{50}$ ASCT1 (µM) | IC$_{50}$ ASCT2 (µM) | LTP Threshold (µM) |
|---|---|---|---|---|
| L-serine | 94 | 292 | 822 | NA |
| D-serine | 2592 | 3937 | 4913 | 3 |
| L-glutamine | 41* 4713* | 3373 | 541 | NA |
| L-asparagine | 108 | 656 | 674 | 3 |
| L-GPNA | 57* 4135* | >10,000 | 1133 | 100 |
| L-4-fluorophenylglycine | 83.3 | 377 | 437 | 0.3 |
| L-4-hydroxyphenylglycine | 283 | 1322 | 1728 | 10 |
| DL-2-fluorophenylglycine | 1572 | >3000 | >3000 | >300 |
| L-phenylglycine | 228 | 1217 | 945 | 10 |
| L-proline | 1780 | 2139 | >10,000 | NA |
| L-trans-4-hydroxyproline | 16* 3047* | 188 | 3475 | 3 |
| L-cyclopropylglycine | 180 | 948 | 428 | 1 |

* values for high and low affinity components

NA = not applicable

| Compound | Component 1 IC$_{50}$ µM | Component 2 IC$_{50}$ µM | Component 1 Fraction (%) |
|---|---|---|---|
| L-glutamine | 26.9 | 2737 | 36.7 |
| L-t-4OHPro | 17.2 | 2989 | 61.1 |

Figure 6A: Transport of [³H]D-serine by HEK cells expressing ASCT1 (SLC1A4) and ASCT2 (SLC1A5). The sodium-dependent transport of D-serine was similar in both cell lines.
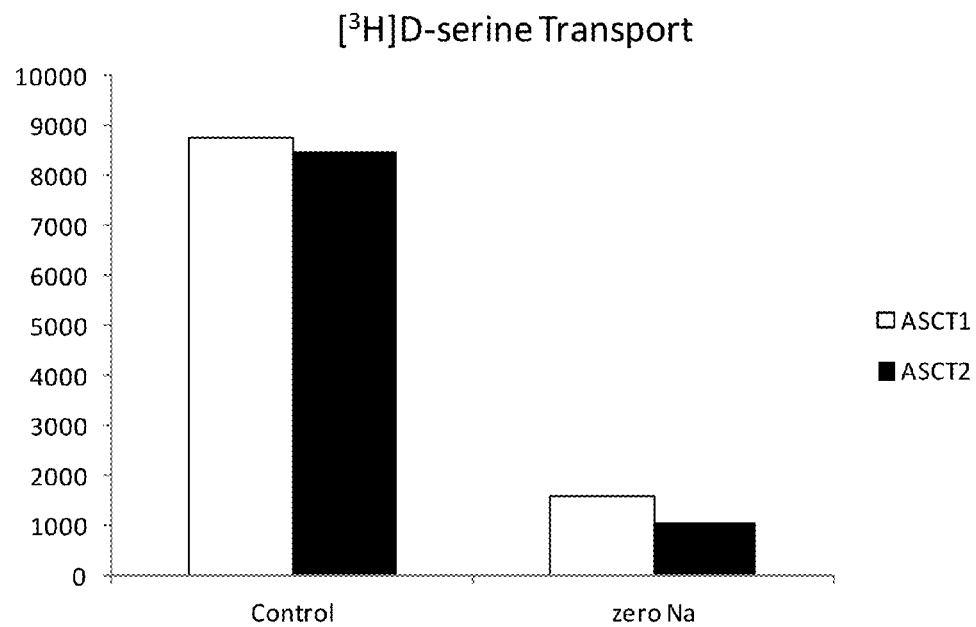

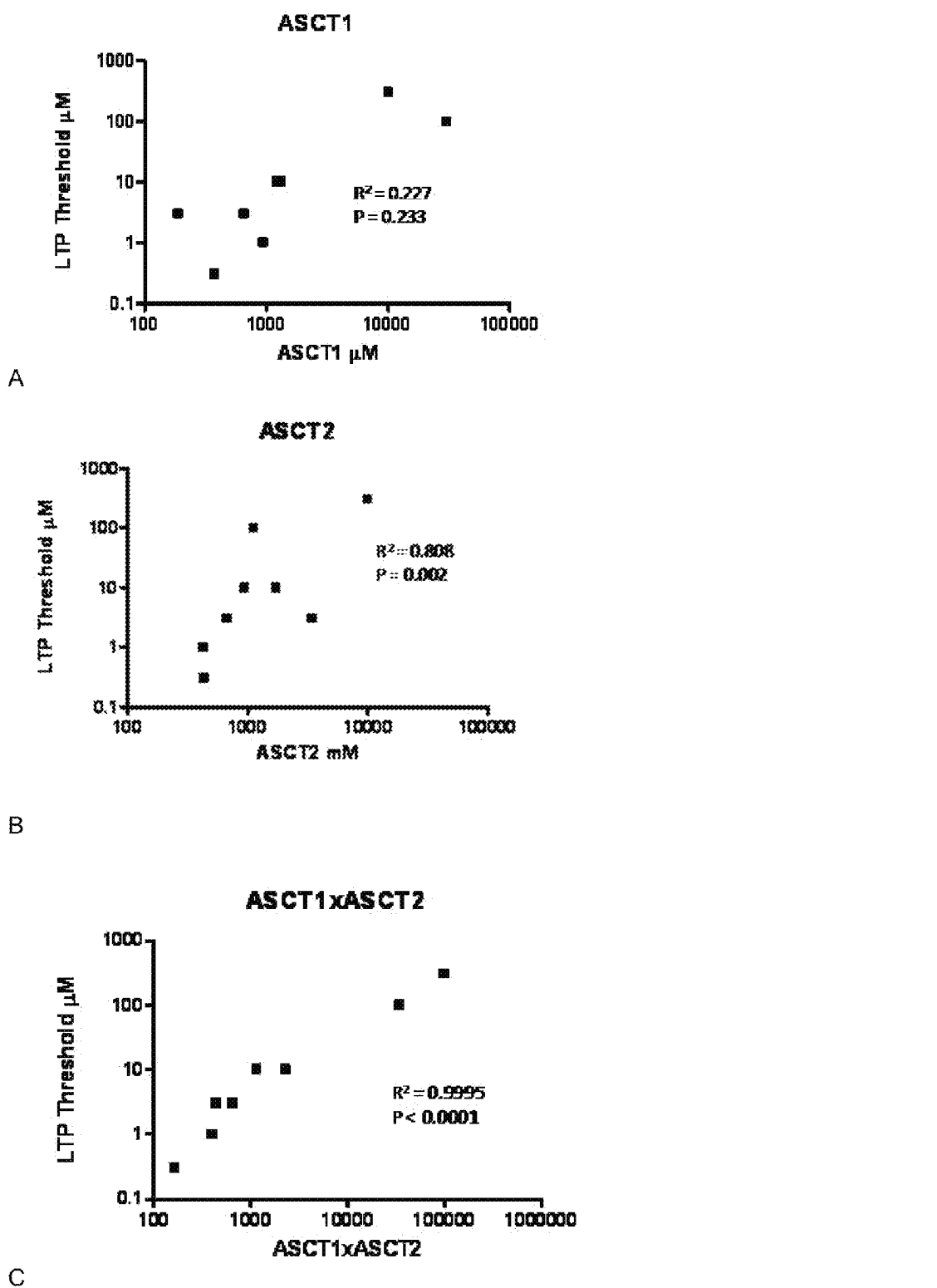
Figure 7: Correlations between the ability of compounds to inhibit transport in HEK cells expressing ASCT1 and ASCT2 and the threshold concentration for LTP enhancement in the visual cortex Figure 9
A
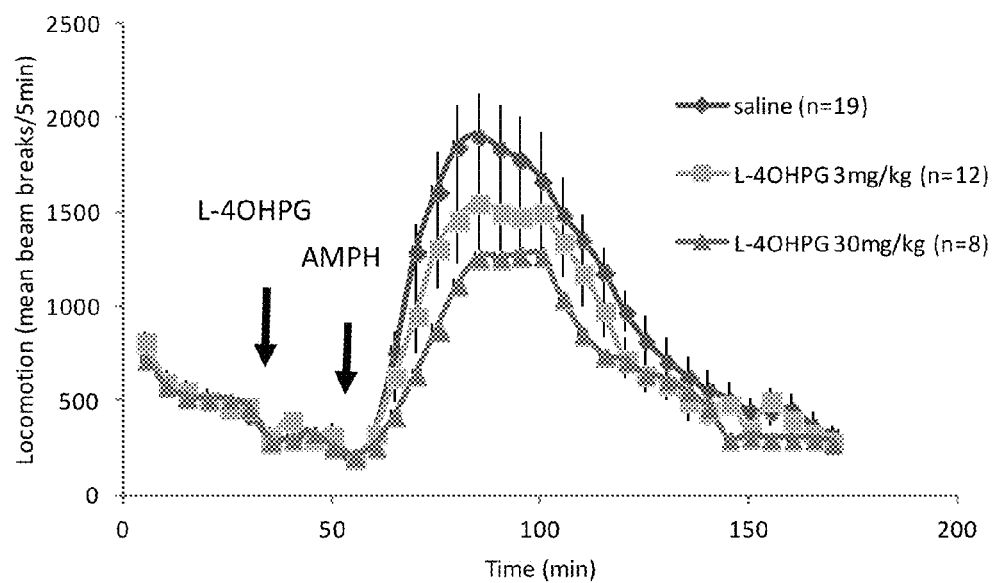
B
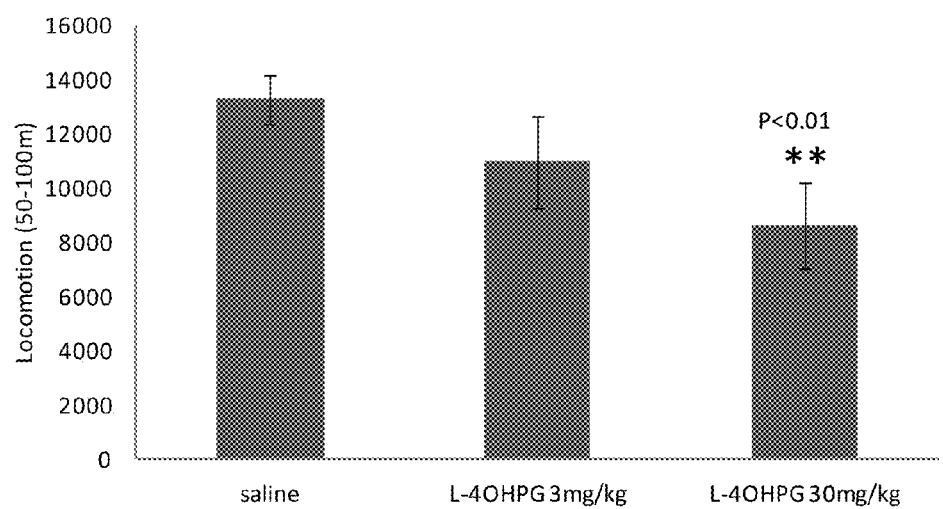

Figure 10
A
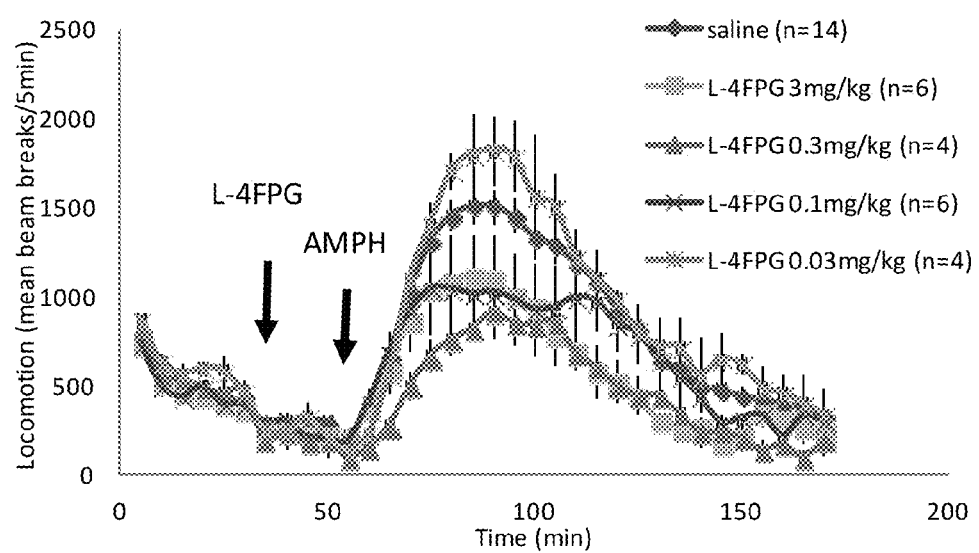
B
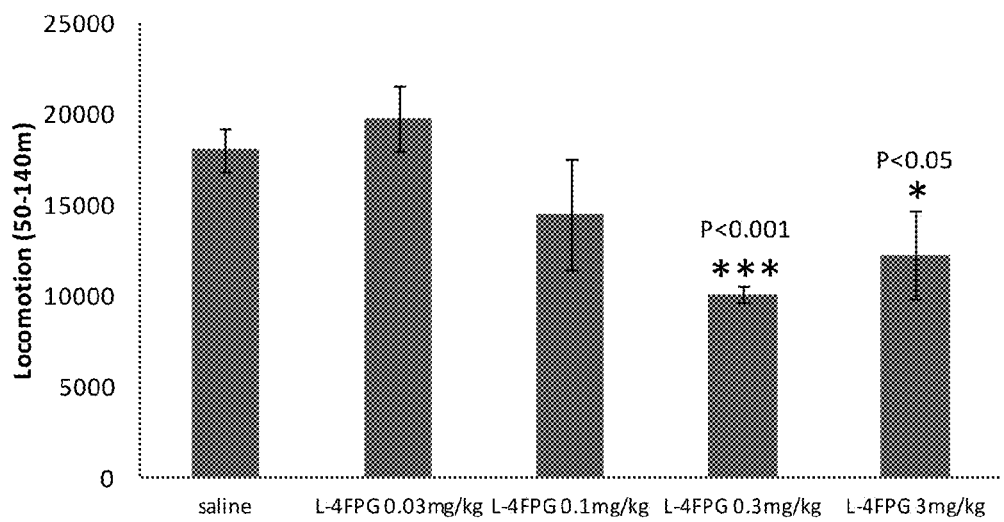

Figure 11: Effects of R-gamma (2,4 dichloro benzy)-L-proline (DCBPro) on amphetamine-induced hyperactivity in mice
A
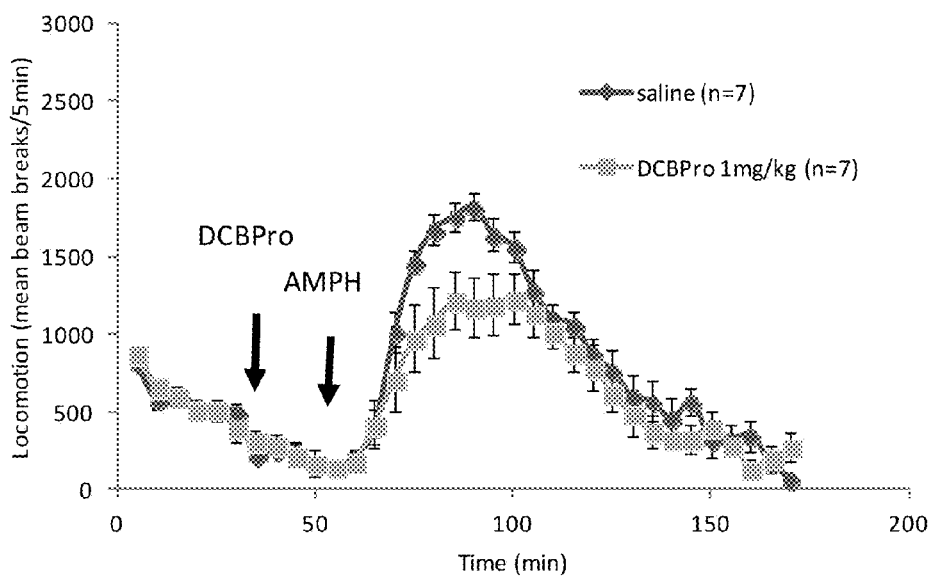
B
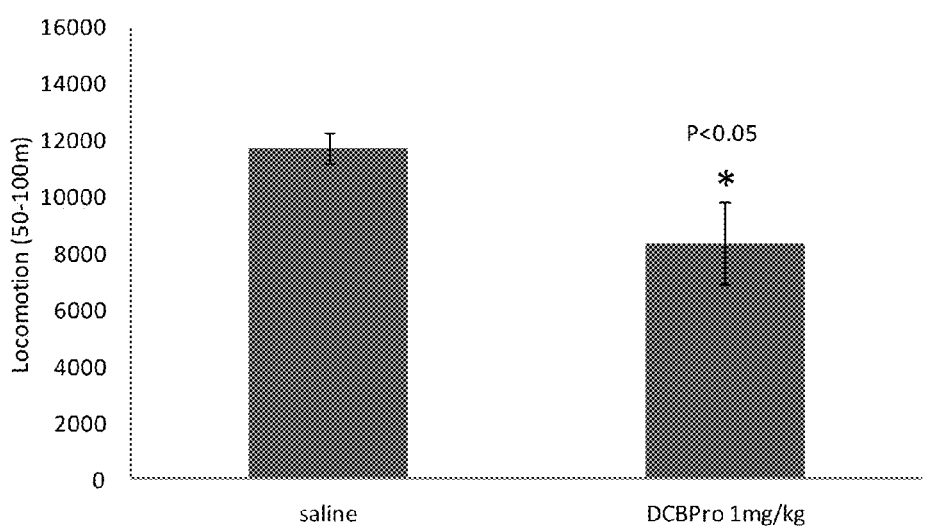

Figure 12
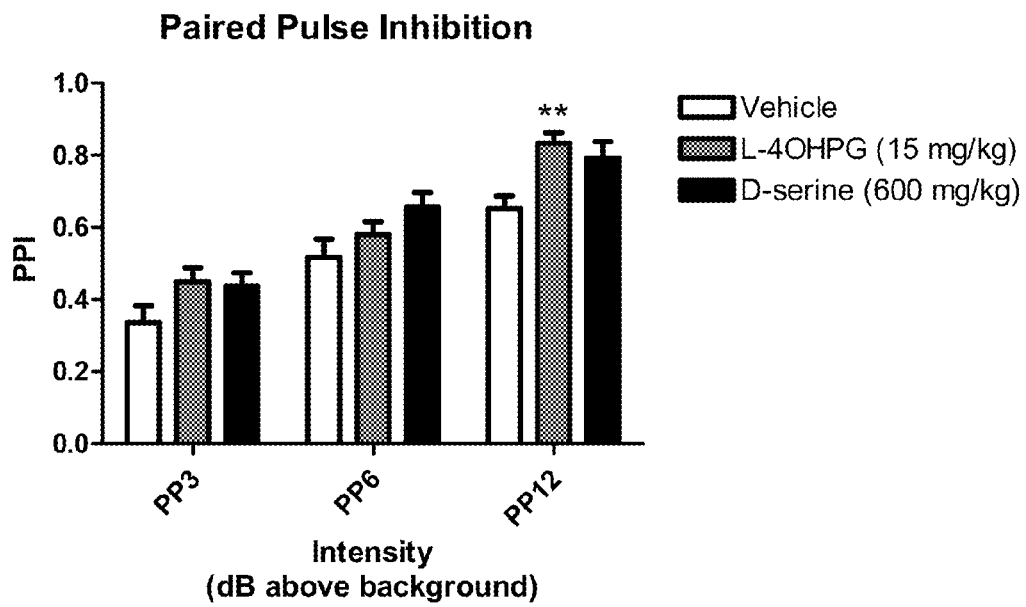
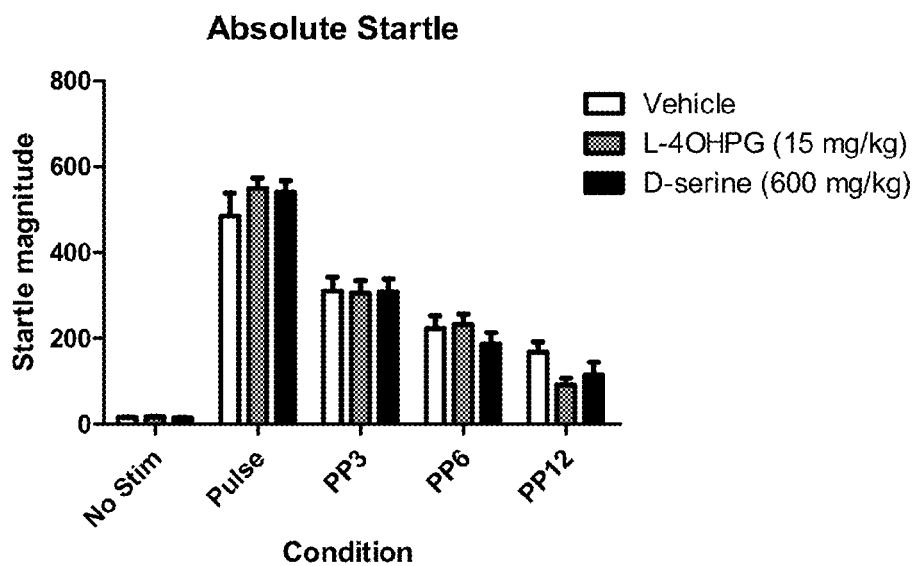

D-SERINE TRANSPORTER INHIBITORS AS PHARMACEUTICAL COMPOSITIONS FOR THE TREATMENT OF CENTRAL NERVOUS SYSTEM DISORDERS

CROSS-REFERENCE TO RELATED APPLICATION

This application is based, and claims priority under 35 U.S.C. §120 to U.S. Provisional Patent Application No. 61/490,652 filed on May 27, 2011, and which is incorporated herein by reference.

FIELD OF THE INVENTION

The present invention relates to pharmaceutical compositions comprising D-serine transporter inhibitors and therapeutic methods using such pharmaceutical compositions in methods for the treatment of central nervous system disorders.

BACKGROUND

Neuronal circuits in the central nervous system rely on the release of chemical neurotransmitters from specialized connections called synapses for communication. The major excitatory neurotransmitter is the amino acid glutamate, and release of glutamate from a pre-synaptic terminal elicits a response through activation of several types of receptors. One of the sub-types of glutamate receptors, the N-methyl-D-aspartate (NMDA) receptor, plays a major role in neuronal communication and in the plasticity of synaptic responses that occurs under both physiological and pathophysiological conditions.

NMDA receptors are ligand-gated cation channels comprised of a tetrameric assembly of NR1, NR2 and NR3 subunits (Paoletti and Neyton, 2007). They are unique amongst neurotransmitter receptors in that they require occupation of two separate recognition sites for activation. An acidic amino acid site where glutamate binds is located on the NR2 subunits, and a neutral amino acid (or co-agonist) site is located on the NR1 sub-unit. The endogenous co-agonist for this site was originally thought to be glycine, but more recent evidence indicated that D-serine is also an endogenous co-agonist. In fact, in higher brain regions D-serine may be the dominant co-agonist. Occupation of the co-agonist site is essential for glutamate (or a glutamate analog) to activate the NMDA receptor, and in native assays the removal of glycine or D-serine by exogenously-applied degradative enzymes can reduce or abolish NMDA receptor-mediated responses. For example, in the rat hippocampal slice, application of the D-serine metabolizing enzyme, D-amino acid oxidase (D-AAO), completely prevents the induction of long-term potentiation (LTP) a form of synaptic plasticity whose initiation is dependent on NMDA receptor activation (Yang et al., 2003). This suggests that the dominant co-agonist in this case is D-serine, since glycine is not a substrate for D-AAO.

The mechanisms that regulate extracellular D-serine, and therefore govern how NMDA receptors are activated, are not well understood. In keeping with other neurotransmitters and neuromodulators, it is likely that transporters on the cell surface are involved in regulating synaptic levels of D-serine. Amino acid transporters usually prefer L-amino acids, however D-serine has been shown to be a substrate for certain transporters. These include the heterodimeric transporter asc-1 (SLC3A2/SLC7A10) which has micromolar affinity for D-serine, ASCT2 (SLC1A5), ATB$^{O+}$ (SLC7A9) and PAT1-4 (SLC36A1-4). Based on the tissue and cellular localization, the primary candidates for transporters that regulate synaptic D-serine levels are asc-1 (neuronal) and ASCT2 (glial). The related transporter ASCT1 (SLC1A4) also has been localized to neurons and glia, however it has been reported that D-serine is not a substrate for ASCT1 (Shafqat et al., 1993). None of these transporters are selective for D-serine, and their substrates are typically small neutral amino acids such as serine, alanine, cysteine and threonine. They also are known to function as exchangers that can flux their substrates both into and out of cells. Consequently, it has been unclear if these transporters are responsible primarily for the net uptake or the net release of D-serine and other substrates. Considering that asc-1 has the highest known affinity for D-serine, it has been thought that this transporter is primarily responsible for removing D-serine from the extracellular space (Rutter et al., 2007). In support of this, the asc-1 knock-out mouse has a phenotype that includes increased excitability (Xie et al., 2005).

In the CNS, NMDA receptors are important mediators of glutamate-mediated neurotransmission and synaptic plasticity. NMDA receptors occur throughout the brain and spinal cord and are widely considered to be essential for neuronal physiology (Traynelis et al, 2010). Based on experiments using exogenously-applied D-AAO, D-serine has been shown to be an endogenous co-agonist involved in NMDA-receptor-mediated synaptic responses in the forebrain (Henneberger et al, 2010; Fossat et al, 2012). In many regions of the CNS, NMDA receptors mediate the phenomenon of long-term potentiation (LTP), an important form of synaptic plasticity. NMDA receptor-dependent LTP is viewed as a mechanism of synaptic strengthening that is fundamental to the establishment and maintenance of appropriate synaptic connections. In the hippocampus, for example, LTP has been studied as a synaptic substrate of learning and memory (Citri and Malenka, 2007).

Certain CNS disorders are associated with a deficit in NMDA receptor function. In schizophrenia, the NMDA receptor hypofunction hypothesis was formulated to explain the "negative symptoms" and reduced cognitive functions that occur in this mental disorder and which are poorly treated by traditional antipsychotic drugs centered on dopamine. NMDA antagonists such as PCP, ketamine and MK-801 reproduce schizophrenic symptoms in humans, supporting the idea that reduced NMDA receptor function occurs in this disease (Coyle, 2006). Consequently, therapeutic strategies to enhance NMDA receptor function are currently being investigated. One example are inhibitors of transporters for glycine that are responsible for maintaining synaptic glycine concentrations. Since glycine, like D-serine, is an endogenous co-agonist at the NMDA receptor, inhibition of glycine re-uptake will increase synaptic glycine concentrations and increase NMDA receptor function. Currently, glycine transport inhibitors are in late stage clinical studies for the treatment of schizophrenia (Field et al, 2011). D-serine itself has been examined in several small schizophrenia trials as an adjunctive therapy with antipsychotic drugs (Labrie and Roder, 2010), with positive results. Consequently, the D-serine transport modulators described here are expected to be of utility in the treatment of schizophrenia, and we provide preclinical support for this idea. In addition, compounds that have the ability to enhance LTP have been shown to improve cognition in human subjects (Lynch et al, 2011). We show here that D-serine transport modulation enhances LTP not only in the visual cortex, but also in hippocampus, a region of the brain associated with learning and memory. Consequently, D-serine transport modulators will be useful as cognitive enhancing agents and can be used to treat diseases such as Alzheimer's disease or any CNS disorder where cognitive abilities are impaired.

SUMMARY OF THE INVENTION

The present invention relates to the use of pharmaceutical compositions comprising D-serine transporter inhibitor compound(s) in methods for the treatment of central nervous system (CNS) disorders.

D-serine transport inhibitors may be used to treat schizophrenia, schizophreniform disorder, and schizoaffective disorder and specifically conditions selected from the following: conduct disorder, solitary aggressive type conduct disorder, undifferentiated type tourette's disorder chronic motor or vocal tic disorder transient tic disorder tic disorder alcohol withdrawal delirium alcohol hallucinosis alcohol dementia associated with alcoholism, amphetamine or similarly acting sympathomimetic intoxication, amphetamine or similarly acting sympathomimetic delirium, amphetamine or similarly acting sympathomimetic delusional disorder, cannabis delusional disorder, cocaine intoxication, cocaine delirium, cocaine delusional disorder, hallucinogen hallucinosis, hallucinogen delusional disorder, hallucinogen mood disorder, hallucinogen post-hallucinogen perception disorder, phencyclidine or similarly acting arylcyclohexylamine intoxication, phencyclidine or similarly acting arylcyclohexylamine delirium, phencyclidine or similarly acting arylcyclohexylamine delusional disorder, phencyclidine or similarly acting arylcyclohexylamine mood disorder, phencyclidine or similarly acting arylcyclohexyilamine organic mental disorder, other or unspecified psychoactive substance intoxication, other or unspecified psychoactive substance delirium, other or unspecified psychoactive substancedementia, other or unspecified psychoactive substance delusional disorder, other or unspecified psychoactive substance hallucinosis, other or unspecified psychoactive substance mood disorder, other or unspecified psychoactive substance anxiety disorder, other or unspecified psychoactive substance personality disorder, other or unspecified psychoactive substance organic mental disorder, delirium, dementia, organic delusional disorder, organic hallucinosis, organic mood disorder, organic anxiety disorder, organic personality disorder, organic mental disorder, obsessive compulsive disorder, post-traumatic stress disorder, generalized anxiety disorder, anxiety disorder, body dysmorphic disorder, hypo-chondriasis (or hypochondriacal neurosis), somatization disorder, undifferentiated somatoform disorder, somatoform disorder, intermittent explosive disorder, kleptomania, pathological gambling, pyromania, trichotillomania, and impulse control disorder, schizophrenia, catatonic, subchronic, schizophrenia, catatonic, chronic, schizophrenia, catatonic, sub chronic with acute exacerbation, schizophrenia, catatonic, chronic, with acute exacerbation, schizophrenia, catatonic, in remission, schizophrenia, catatonic, unspecified, schizophrenia, disorganized, subchronic, schizophrenia, disorganized, chronic, schizophrenia, disorganized, subchronic with acute exacerbation, schizophrenia, disorganized, chronic with acute exacerbation, schizophrenia, disorganized, in remission, schizophrenia, disorganized, unspecified, schizophrenia, paranoid, subchronic, schizophrenia, paranoid, chronic, schizophrenia, paranoid, sub chronic with acute exacerbation, schizophrenia, paranoid, chronic with acute exacerbation, schizophrenia, paranoid, in remission, schizophrenia, paranoid, unspecified, schizophrenia, undifferentiated, subchronic, schizophrenia, undifferentiated, chronic, schizophrenia, undifferentiated, sub chronic with acute exacerbation, schizophrenia, undifferentiated, chronic with acute exacerbation, schizophrenia, undifferentiated, in remission, schizophrenia, undifferentiated, unspecified, schizophrenia, residual, subchronic, schizophrenia, residual, chronic, schizophrenia, residual, subchronic with acute exacerbation, schizophrenia, residual, chronic with acute exacerbation, schizophrenia residual in remission, schizophrenia, residual, subchronic schizophrenia, residual, chronic, schizophrenia, residual, subchronic with acute exacerbation, schizophrenia, residual, chronic with acute exacerbation, schizophrenia, residual, in remission, schizophrenia, residual, unspecified, delusional (paranoid) disorder, brief reactive psychosis, schizophreniform disorder, schizoaffective disorder, induced psychotic disorder, psychotic disorder (atypical psychosis), personality disorders, paranoid, personality disorders, schizoid, personality disorders, schizotypal, personality disorders, antisocial, and personality disorders, borderline.

D-serine transport inhibitors may be used to treat a patient suffering from one or more types of cognitive disorder, such as agnosia, amnesia, aphasia, apraxia, delirium, dementia, and a learning disorder.

To "treat," as used here, means to deal with medically. It includes, for example, administering a compound of the invention to prevent the onset of a cognitive disorder, to alleviate its severity, and to prevent its reoccurrence.

The term "cognitive disorder," as used here, means any condition characterized by a deficit in mental activities associated with thinking, learning, or memory. Examples of such disorders include agnosias, amnesias, aphasias, apraxias, deliriums, dementias, and learning disorders.

In some cases, the cause of a cognitive disorder may be unknown or uncertain. In other cases, the cognitive disorder may be associated with (that is, be caused by or occur in the loss of neurons or other structures involved in the transmission of signals between neurons. Hence, cognitive disorders may be associated with neurodegenerative diseases such as Alzheimer's disease, corticobasal degeneration, Creutzfeldt-Jacob disease, frontotemporal lobar degeneration, Huntington disease, multiple sclerosis, normal pressure hydrocephalus, organic chronic brain syndrome, Parkinson's disease, Pick disease, progressive supranuclear palsy, or senile dementia (Alzheimer type); it may be associated with trauma to the brain, such as that caused by chronic subdural hematoma, concussion, intracerebral hemorrhage, or with other injury to the brain, such as that cause by infection (e.g., encephalitis, meningitis, septicemia) or drug intoxication or abuse.

Cognitive disorders may also be associated with other conditions which impair normal functioning of the central nervous system, including psychiatric disorders such as anxiety disorders, dissociative disorders, mood disorders, schizophrenia, and somatoform and factitious disorders; it may also be associated with conditions of the peripheral nervous system, such as chronic pain.

D-serine transport inhibitors may be used to treat agnosias, amnesias, aphasias, apraxias, deliriums, dementias, learning disorders and other cognitive disorders regardless of whether their cause is known or not.

Examples of dementias which may be treated with the methods of the invention include AIDS dementia complex, Binswanger's disease, dementia with Lewy Bodies, frontotemporal dementia, multi-infarct dementia, Pick's disease, semantic dementia, senile dementia, and vascular dementia.

Examples of learning disorders which may be treated with the methods of the invention include Asperger's syndrome, attention deficit disorder, attention deficit hyperactivity disorder, autism, childhood disintegrative disorder, and Rett syndrome.

Examples of aphasia which may be treated with the methods of the invention include progressive non-fluent aphasia. The compounds described here may also be used to treat patients having deficits in mental activities that are mild or that otherwise do not significantly interfere with daily life. Mild cognitive impairment is an example of such a condition: a patient with mild cognitive impairment displays symptoms of dementia (e.g., difficulties with language or memory) but the severity of these symptoms is such that a diagnosis of dementia may not be appropriate. The compounds described here may be used to treat mild cognitive impairment and other, similarly less severe forms of cognitive disorders.

DESCRIPTION OF THE DRAWINGS

FIG. 1 shows the ability of selected amino acids to inhibit D-serine transport into neurons (rat brain synaptosomes) and glia (rat hippocampal astrocytes). Values are the concentration of amino acid required to inhibit 50% of [$^3$H]D-serine transport ($IC_{50}$) in µM, and are the means of at least two determinations. L-GPNA: L-γ-nitrophenyl glutamyl anilide.

FIG. 1B represents a graph featuring summary data showing the dose-dependent effects of L-4OHPG on $EPSC_{NMDA}$.

FIG. 6A represents a graph that shows transport of [$^3$H]D-serine into HEK cells expressing ASCT1 or ASCT2. Transport was measured in the presence (control) and in the absence (zero Na) of extracellular sodium.

FIG. 2 shows $IC_{50}$ values for the inhibition of [$^3$H]L-serine transport into astrocytes and HEK cells expressing recombinant human ASCT1 or ASCT2. Values are $IC_{50}$'s in µM from 6-12 point inhibition curves, with an n of at least 2. For L-trans-4-hydroxyproline (L-t-4OHPro) and L-GPNA, two components of inhibition were present in the astrocyte assay, and *values are presented for the high and low affinity components. For comparison, threshold concentrations for the enhancement of LTP in rat visual cortex slices are shown.

FIG. 7 represents the correlation of the $IC_{50}$ values from the transport assays (see Table 2 and accompanying explanation) with the LTP threshold data (see FIG. 2A and accompanying explanation). Graph A shows the correlation between the $IC_{50}$ values for the ASCT1 transporter (also known as SLC1A4) and the LTP threshold data; graph B shows the correlation between the $IC_{50}$ values for the ASCT2 transporter (also known as SLC1A5) and the LTP threshold data; graph C shows the correlation between the product of both ASCT1's and ASCT2's $IC_{50}$ values and the LTP threshold data in order to take into account how contributions from both transporters might be important to produce the LTP enhancement (this plot gives the best correlation and suggests that inhibition of both transporters, leads to optimal LTP enhancement).

FIG. 9 represents a graph showing that L-4OHPG reduces amphetamine-induce hyperlocomotion in mice, a model of schizophrenia. (A) activity counts over time between saline and drug-treated groups. (B) total activity measured between 50 and 100 minutes for the saline and drug-treated groups.

FIG. 10 represents a graph showing that L-4FPG reduces amphetamine-induce hyperlocomotion in mice, a model of schizophrenia. (A) activity counts over time between saline and drug-treated groups. (B) total activity measured between 50 and 100 minutes for the saline and drug-treated groups.

FIG. 11 represents a graph showing that R-gamma (2,4 dichloro benzyl)-L-proline (DCBPro) reduces amphetamine-induce hyperlocomotion in mice, a model of schizophrenia. (A) activity counts over time between saline and drug-treated groups. (B) total activity measured between 50 and 100 minutes for the saline and drug-treated groups.

FIG. 12 represents a graph showing that L-4OHPG has a significant effect on paired pulse inhibition in the mouse, a model of schizophrenia. (A) Effects of D-serine (600 mg/kg) and L-4OHPG (15 mg/kg) on PPI at three different intensities. (B) lack of effect of D-serine (600 mg/kg) and L-4OHPG (15 mg/kg) on startle response.

DETAILED DESCRIPTION OF THE INVENTION

Figure 1A:
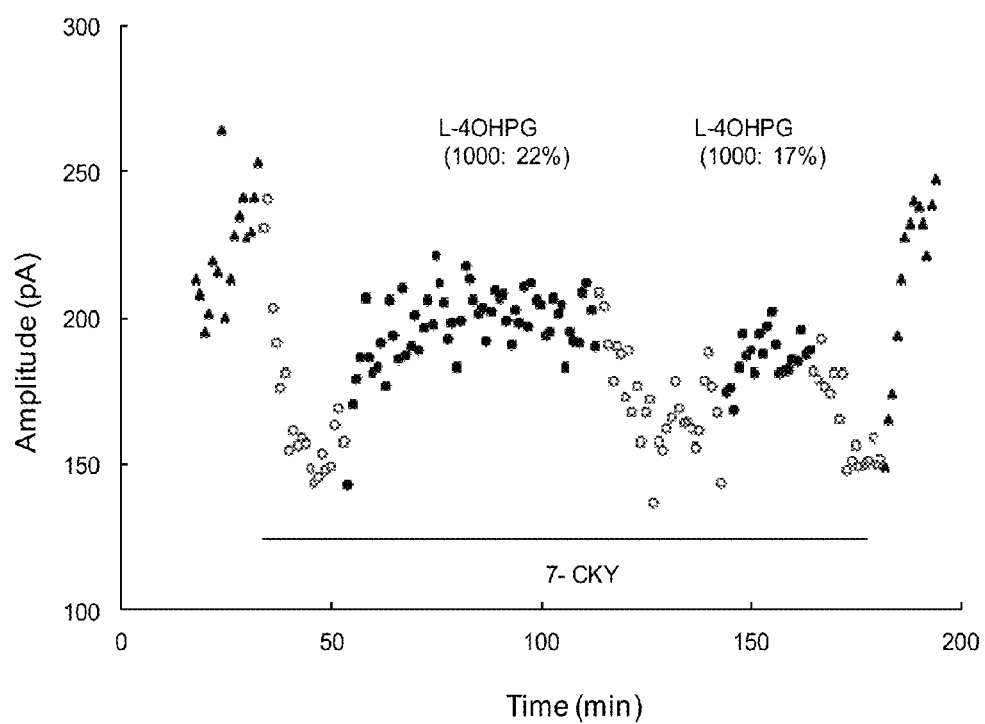
FIG. 1A represents a graph displaying the electrophysiological recording from rat hippocampal slices and showing that L-4OHPG (L-4-hydroxyphenylglycine) potentiates NMDA receptor-mediated excitatory postsynaptic currents ($EPSC_{NMDA}$). The representative experiment shows that the potentiation effect of L-4OHPG (1000 µM) lasted for one hour and then returned to baseline in control buffer. 1000 is the concentration of L-4OHPG in µM and 22% refers to the percentage increase in the amplitude of $EPSC_{NMDA}$. Dots represent the amplitudes of $EPSC_{NMDA}$ Filled triangles represent control; open circles represent 1 µM 7-CKY and filled circles represent 1000 µM L-4OHPG. 7-CKY is a competitive inhibitor at the D-serine site of the NMDA receptor, which inhibits the NMDA receptor-mediated EPSCs and increases the sensitivity of $EPSC_{NMDA}$ to D-serine.

In one aspect the invention relates to a method for the treatment of central nervous system disorders caused by a deficit in N-methyl-D-aspartate receptor function, the method comprising administering to a subject in need thereof an acceptable pharmaceutical composition containing a therapeutically effective amount of one or more D-serine transporter inhibitor compounds.

In another aspect the invention relates to a method for the treatment of central nervous system disorders, the method comprising administering to a subject in need thereof an acceptable pharmaceutical composition containing a therapeutically effective amount of one or more D-serine transporter inhibitor compounds selected from the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family.

In another aspect the invention relates to a method for the treatment of central nervous system disorders, the method comprising administering to a subject in need thereof an acceptable pharmaceutical composition containing a therapeutically effective amount of one or more D-serine transporter inhibitor compounds selected from L-gamma-glutamyl-4-nitroanilide, L-4-hydroxyphenylglycine, L-4-fluorophenylglycine, L-phenylglycine, trans-4-hydroxy-L-proline and R-gamma-2,4,-dichlorobenzyl-L-proline.

In another aspect the invention relates to a pharmaceutical composition comprising as active ingredient a therapeutically effective amount of at least one D-serine transporter inhibitor compound and a pharmaceutically acceptable adjuvant, diluents or carrier.

In another aspect the invention relates to a method for the treatment of central nervous system disorders caused by a deficit in N-methyl-D-aspartate receptor function, the method comprising administering to a subject in need thereof an acceptable pharmaceutical composition containing a therapeutically effective amount of at least one or more ASCT1 inhibitor compounds and/or at least one or more ASCT1 inhibitor compounds.

In another aspect the invention relates to a pharmaceutical composition comprising as active ingredient a therapeutically effective amount of at least one or more ASCT1 inhibitor and/or at least one or more ASCT2 inhibitor and a pharmaceutically acceptable adjuvant, diluents or carrier.

In another aspect the invention relates to a pharmaceutical composition comprising as active ingredient a therapeutically effective amount of L-gamma-glutamyl-4-nitroanilide and a pharmaceutically acceptable adjuvant, diluents or carrier for the treatment of central nervous system disorders.

In another aspect the invention relates to a pharmaceutical composition comprising as active ingredient a therapeutically effective amount of L-4-hydroxyphenylglycine and a pharmaceutically acceptable adjuvant, diluents or carrier for the treatment of central nervous system disorders.

In another aspect the invention relates to a pharmaceutical composition comprising as active ingredient a therapeutically effective amount of L-4-fluorophenylglycine and a pharmaceutically acceptable adjuvant, diluents or carrier for the treatment of central nervous system disorders.

In another aspect the invention relates to a pharmaceutical composition comprising as active ingredient a therapeutically effective amount of L-phenylglycine and a pharmaceutically acceptable adjuvant, diluents or carrier for the treatment of central nervous system disorders.

In another aspect the invention relates to a pharmaceutical composition comprising as active ingredient a therapeutically effective amount of trans-4-hydroxy-L-proline and a pharmaceutically acceptable adjuvant, diluents or carrier for the treatment of central nervous system disorders.

In another aspect the invention relates to a pharmaceutical composition comprising as active ingredient a therapeutically effective amount of R-gamma-2,4-dichlorobenzyl-L-proline and a pharmaceutically acceptable adjuvant, diluents or carrier for the treatment of central nervous system disorders.

In another aspect, the present invention relates to pharmaceutical compositions comprising D-serine transporter inhibitors and therapeutic methods using such pharmaceutical compositions in methods for the treatment of central nervous system disorders.

In another aspect, the present invention relates to a method for the treatment of central nervous system disorders comprising administration of one or more D-serine transporter inhibitors by different administration routes. D-serine transporter inhibitors were identified as compounds that inhibit transport mechanisms in neurons and astrocytes, in D-serine transport assays in vitro.

In another aspect the present invention relates to a pharmaceutical composition comprising a therapeutically effective amount of at least one D-serine transporter inhibitor compound, said compound being present alone or in combination with one or more pharmaceutically acceptable excipients.

In another aspect the present invention relates to a method for the treatment of central nervous system disorders caused by a deficit in N-methyl-D-aspartate receptor function, the method comprising administering to a subject in need thereof an acceptable pharmaceutical composition containing a therapeutically effective amount of one or more D-serine transporter inhibitor compounds.

In another aspect the present invention relates to a pharmaceutical composition comprising a therapeutically effective amount of at least one compound selected from the group consisting of ASCT1 inhibitor, ASCT2 inhibitor, and combinations thereof, said compound being present alone or in combination with one or more pharmaceutically acceptable excipients.

In another aspect the present invention relates to a method for the treatment of central nervous system disorders caused by a deficit in N-methyl-D-aspartate receptor function, the method comprising administering to a subject in need thereof an acceptable pharmaceutical composition containing a therapeutically effective amount of one or more compounds selected from the group consisting of ASCT1 inhibitor, ASCT2 inhibitor, and combinations thereof.

In another aspect the present invention relates to a method for the treatment of central nervous system disorders, the method comprising administering to a subject in need thereof an acceptable pharmaceutical composition containing a therapeutically effective amount of one or more compounds selected from the group consisting of ASCT1 inhibitor, ASCT2 inhibitor, and combinations thereof.

In another aspect the present invention relates to a method for the treatment of central nervous system disorders caused by a deficit in N-methyl-D-aspartate receptor function, the method comprising administering to a subject in need thereof an acceptable pharmaceutical composition containing a therapeutically effective amount of L-gamma-glutamyl-4-nitroanilide L-4-hydroxyphenylglycine, L-4-fluorophenylglycine, L-phenylglycine, trans-4-hydroxy-L-proline and R-gamma-2,4-dichlorobenzyl-L-proline.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, front of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

D-serine transporter inhibitor compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

An acceptable pharmaceutical composition is one that can be administered by any route to a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the pharmaceutical composition.

The claimed pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Reminton's Pharmaceutical Sciences, Mack Publishing Company, Easton, Pa., 16$^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like.

Examples mentioned herein are not intended to limit the scope of the invention in any way.

Using D-serine transport assays in vitro, we have identified compounds that inhibit transport mechanisms in neurons and astrocytes. In Table 1, the activities of amino acid analogs to inhibit D-serine transport are shown. Under the assay conditions used, the sodium-independent transport of D-serine by rodent forebrain synaptosomes is mediated by asc-1 (Rutter et al., 2007), and the sodium-dependent transport of D-serine into astrocytes in culture is mediated by an ASCT transporter, ASCT2 according to the literature (Ribeiro et al., 2002).

The data from Table 1 shows that transport of D-serine into neurons and into astrocytes can be pharmacologically distinguished. Analogs of glutamine, phenylglycine, asparagine, cysteine and proline were able to select between the two transport systems.

To determine the effects of transport inhibition on NMDA receptor function, compounds were tested for their ability to affect NMDA receptor-mediated synaptic responses in brain slice preparations. L-4-hydroxyphenylglycine (L-4OHPG) potentiated NMDA receptor mediated excitatory post-synaptic currents (EPSC's) in the CA1 region of the hippocampus (FIG. 1A and FIG. 1B). In the visual cortex slice, LTP evoked by theta burst stimulation was enhanced by L-4OHPG. L-4OHPG enhanced LTP in a concentration-dependent manner, and its effects were completely prevented by inclusion of D-AAO in the perfusion medium, indicating that its ability to enhance synaptic plasticity was dependent on extracellular D-serine (FIG. 2B). Importantly, none of the compounds identified as D-serine transport inhibitors had significant direct effects on the NMDA receptor (or other glutamate receptor sub-types) as assessed in cultured hippocampal neurons.

Figure 3A:
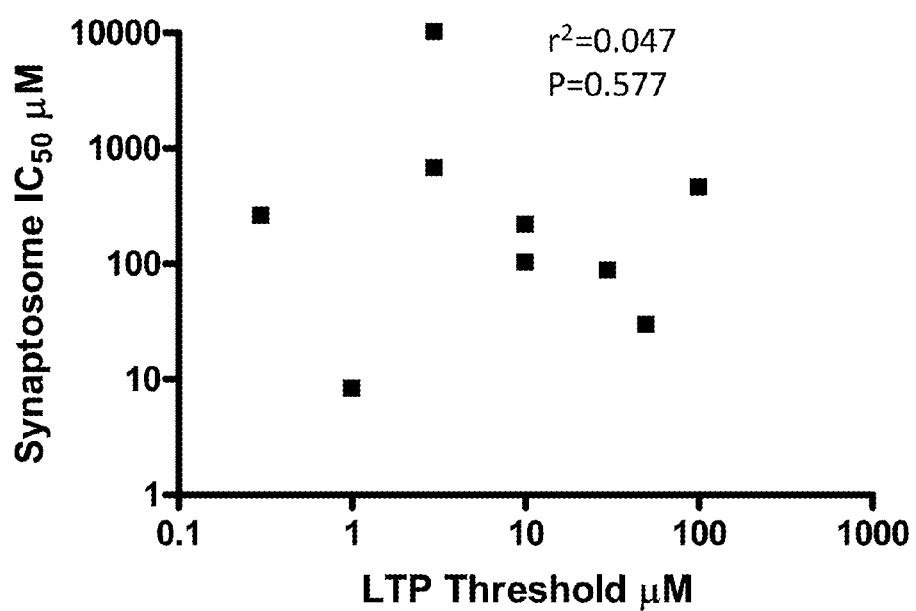
FIG. 3A represents a graph that shows the correlation between the ability of compounds to inhibit neuronal D-serine transport and the threshold concentration required to enhance LTP in the visual cortex slice. The $r^2$ value (correlation coefficient) and p value (probability) indicates that no significant correlation exists.
Figure 3B:
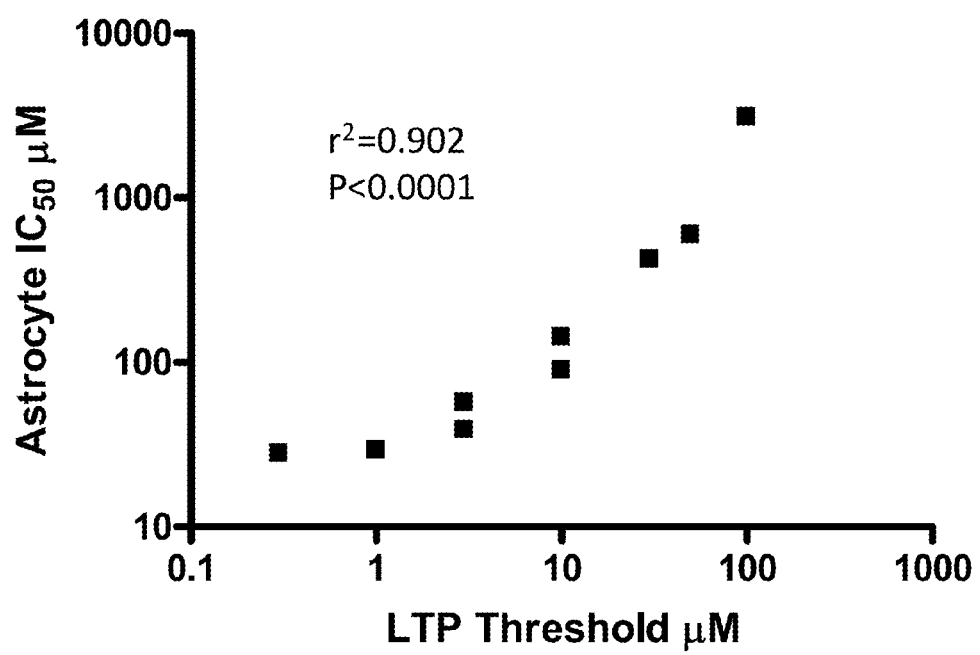
FIG. 3B represents a graph that shows the correlation between the ability of compounds to inhibit astrocyte D-serine transport and the threshold concentration required to enhance LTP in the visual cortex slice. The $r^2$ value (correlation coefficient) and p value (probability) indicates that a highly significant correlation exists.

In an attempt to understand the relative contributions of the neuronal and astrocyte D-serine transporters to the observed ability of compounds to enhance NMDA receptor-mediated responses, correlations were made between the effects of compounds in the transport assays and in the visual cortex slice LTP assay. A poor correlation was found between the effects in the neuronal transport assay and LTP (FIG. 3A, $r^2$=0.047) however an excellent correlation existed between the effects in the astrocyte transport assay and LTP (FIG. 3B, $r^2$=0.902). This indicated that the transporters present in astrocytes are those that regulate extracellular D-serine to influence NMDA receptor-mediated synaptic events.

Figure 4:
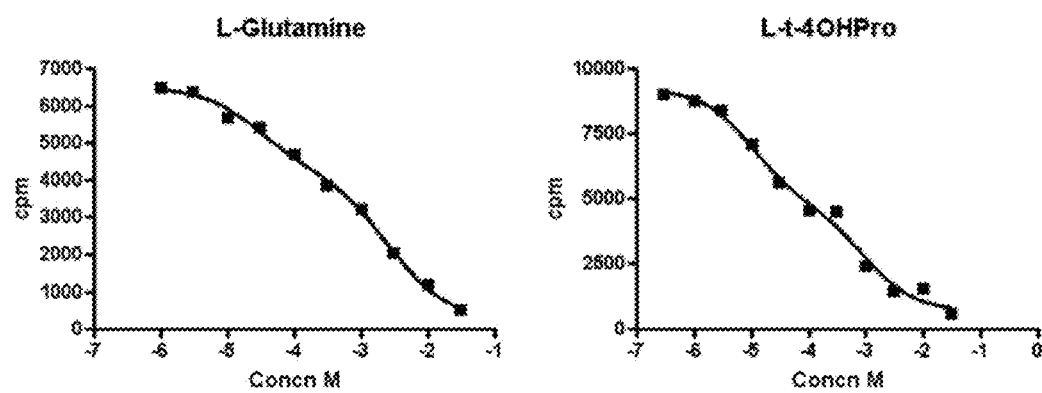
FIG. 4 represents a graph that shows the 2-component inhibition of D-serine transport into astrocytes by L-glutamine and L-trans-4-hydroxyproline (L-t-4OHPro) and $IC_{50}$ values for the individual components. Two-component inhibition curves were fitted using an algorithm available in GraphPad Prism 4. "Component 1" is the high affinity component and "Component 2" is the low affinity component. "Fraction" refers to the proportion that each component contributes to the total inhibition.
Figure 5:
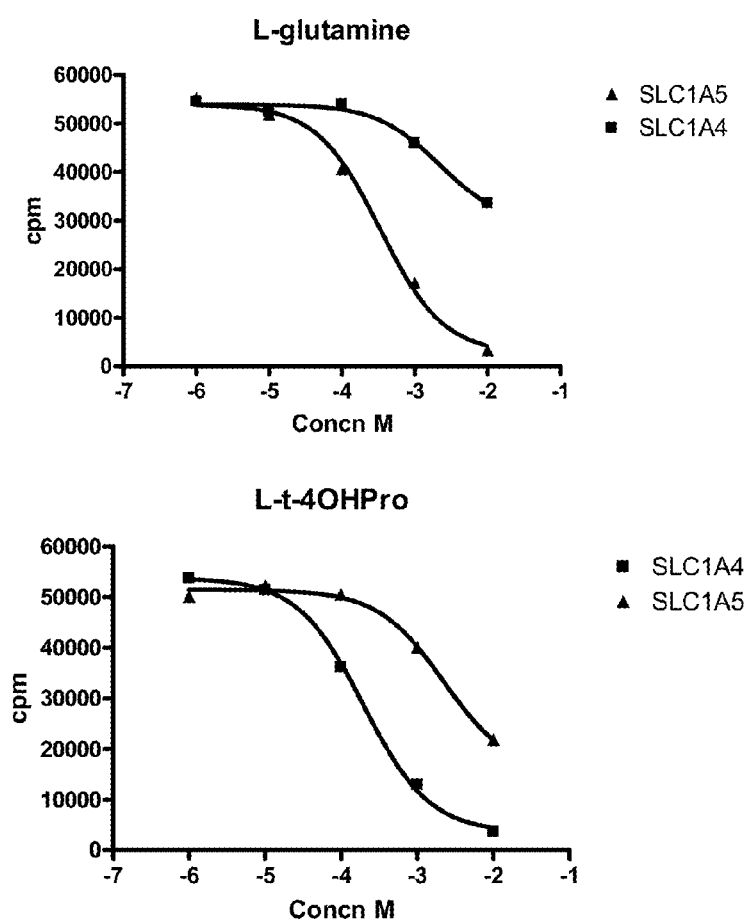
FIG. 5 represents a graph that shows the inhibition of transport into HEK cell lines expressing ASCT1 and ASCT2 by L-glutamine and L-t-4OHPro.
Figure 6B:
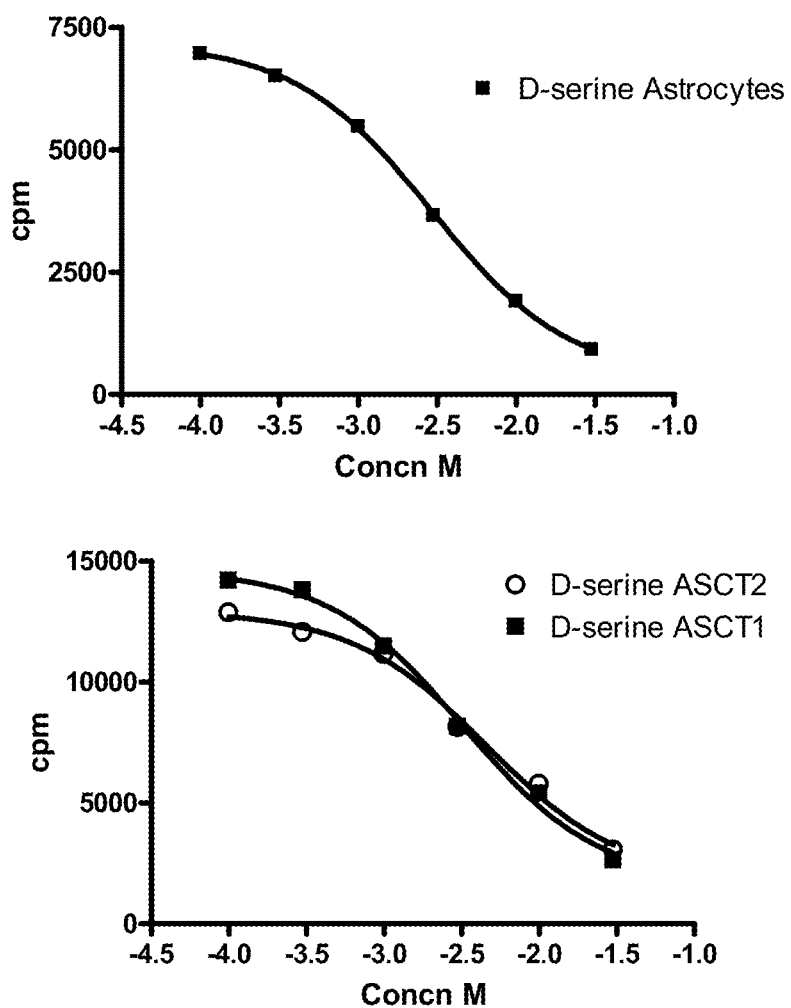
FIG. 6B represents a graph that shows the inhibition of [$^3$H]L-serine transport into astrocytes and HEK cells expressing ASCT1 and ASCT2 by D-serine.

The sodium-dependent D-serine transporter in astrocytes has been reported to be ASCT2 (Ribeiro et al., 2002). In the D-serine transport experiments in astrocytes, we noticed that some compounds produced inhibition curves that exhibited two components, suggesting that more than one transport component was present. In particular, two compounds defined the two components. L-glutamine showed higher affinity for a component that represented approximately 40% of the D-serine transport, and L-trans-4-hydroxyproline (L-t-4OHPro) showed higher affinity for a component that represented approximately 60% of the D-serine transport (FIG. 4). Competition studies with each of these compounds in the presence of the other indicated that L-glutamine had high affinity for the component with low affinity for L-t-4OHPro and vice versa. PCR studies have indicated that both ASCT1 and ASCT2 transporter sub-types are present in astrocytes (Yamamoto et al., 2004). However, functional expression of ASCT1 and ASCT2 in heterologous systems has indicated that, unlike ASCT2, ASCT1 does not transport D-serine (Shafqat et al., 1993). L-glutamine is reported to have high affinity for ASCT2 (range of 23-70 µM; Utsunomiya-Tate et al., 1996; Broer et al., 1999; Torres-Zamorano et al., 1998), and one report indicates that L-t-4OHPro has high affinity for ASCT1 (Pinilla-Tenas et al., 2003). We confirmed the selectivity of L-glutamine and L-t-4OHPro for the ASCT sub-types by examining transport in HEK cells heterologously expressing human ASCT1 and ASCT2. For these experiments, [$^3$H]L-serine was used since it is a high affinity substrate for both sub-types. As shown in FIG. 5, L-glutamine inhibited transport and showed selectivity towards ASCT2, whereas L-t-4OHPro showed selectivity towards ASCT1. Consequently, the two components of transport observed in astrocytes most likely represent ASCT1 (L-t-4OHPro-preferring) and ASCT2 (L-glutamine-preferring). If this is the case, however, it would suggest that ASCT1 does indeed transport D-serine, contrary to the literature report (Pinilla-Tenas et al., 2003). To investigate this, we examined transport into ASCT1-expressing HEK cells. As shown in FIG. 6A, [$^3$H]D-serine was transported into ASCT1-expressing HEK cells in a sodium-dependent manner and to a similar degree to the transport observed in ASCT2-expressing HEK cells. In addition, [$^3$H]L-serine transport was completely inhibited by D-serine in astrocytes and ASCT1 and ASCT2-expressing HEK cell lines (FIG. 6B) as would be expected if D-serine interacts with both transporter sub-types. Consequently, we have discovered that D-serine is indeed a substrate for ASCT1 with an affinity similar to that for ASCT2.

Given this evidence that transport into astrocytes is mediated by both ASCT1 and ASCT2, we needed to determine, which of these transporter sub-types is primarily responsible for the inhibition of D-serine transport that leads to the observed enhancement of LTP. To address this, we examined the ability of the inhibitors identified in the astrocyte transport assay and that enhance LTP to inhibit transport in the HEK cells expressing each ASCT sub-type. As shown in Table 2, L-glutamine and the L-glutamine analog L-gamma-glutamyl-4-nitroanilide (L-GPNA) were selective for ASCT2. L-trans-4OHPro was selective for ASCT1. The phenylglycine analogs, isomers of serine, asparagine and cyclopropylglycine showed equal ability to inhibit both sub-types. Correlations between the IC$_{50}$ values for transport inhibition at the sub-types and the threshold concentrations to enhance LTP revealed no significant correlation with ASCT1 (FIG. 7a) but a significant correlation with ASCT2 (FIG. 7b), however the best correlation was obtained when the contribution of both sub-types was taken into account (product of the IC$_{50}$'s for both ASCT1 and ASCT2; FIG. 7c). This suggests that both sub-types are important for the enhancement of LTP and that dual sub-type inhibitors are the most effective compounds.

Examples of D-serine Transporter Inhibitors

It has been found that certain amino acids of the Glycine/Alanine family, the Glutamine/Asparagine family, the Tryptophan Family, the Phenylglycine family, the Phenylalanine family, the Cysteine family, the Serine/Threonine family, the Cyclic Amino Acid family and the Proline family are examples of D-serine transporter inhibitors.

The following are non-limiting examples of D-serine transporter inhibitors which are useful in the practice of the present invention. The amino acids that were tested for D-serine transport inhibition properties were obtained from Sigma-Aldrich, Tocris Bioscience, Tyger Chemical Scientific, Bachem, ChemBridge Corporation, Matrix Scientific, PI Chemicals Inc., Toronto Research Chemicals and Maybridge Chemicals.

Table of Active Compounds by Amino Acid Family

Criterion for activity: ≥25% inhibition of [$^3$H]D-serine transport into rat hippocampal astrocytes at 1 mM

| Glycine/Alanine Family | |
|---|---|
| Compound | Isomer |
| glycine | |
| alanine | L |
| 2-aminobutyrate | L |
| 2-allylglycine | DL |
| valine | L |
| 3-(methylamino)alanine | L |
| 1-aminocyclopropane-1-carboxylic acid | |
| 1-aminocyclobutane-1-carboxylic acid | |
| 1-aminocyclopentane-1-carboxylic acid | |
| α-cyclopropylglycine | L |
| phenylglycine | L |
| tetrazol-5yl glycine | DL |
| 3-thienylglycine | L |
| aminocyclohexyl acetic acid | L |
| aminofuran-2-yl acetic acid | L |
| amino-(2,3-dihydro-benzo[1,4]dioxin-6-yl)-acetic acid | DL |
| aminonaphthalen-1-yl acetic acid | L |
| aminobicyclo[2.2.1]hept-5-en-2-yl acetic acid | DL |
| dihydrophenylglycine | D |
| 1-adamantyl(amino)acetic acid | |
| 2-aminoadamantine-2-carboxylic acid | |
| 3-benzoylalanine | DL |
| 3-(2-thienyl)-alanine | L |
| 3-cyclopentyl-alanine | L |
| 3(2-naphthyl)-alanine | L |
| 3-benzothienylalanine | L |
| azidohomoalanine | L |
| homopropargylglycine | L |
| valine | L |
| norvaline | L |
| alanine | D |

| Glutamine/Asparagine Family | |
|---|---|
| Compound | Isomer |
| glutamine | L |
| glutamate-γ-hydroxamate | L |
| glutamate-γ-4-nitroanilide | L |
| glutamate-γ-anilide | DL |
| glutamate-γ-(α-naphthylamide) | L |
| glutamate-γ-(β-naphthylamide) | L |
| glutamate-γ-methylester | L |
| glutamate-γ-ethylester | L |
| asparagine | L |
| asparagine | D |
| N-4-phenylasparagine | DL |
| kynurenine | L |
| kynurenine | D |
| 3-hydroxy kynurenine | DL |
| 2-amino-succinic acid 4-ethylester | DL |
| aspartate benzyl ester | L |
| 6-diazo-5-oxo-norleucine | L |

| Tryptophan Family | |
|---|---|
| Compound | Isomer |
| tryptophan | L |
| 6-fluorotryptophan | DL |
| 5-fluorotryptophan | L |
| 4-fluorotryptophan | DL |
| 5-hydroxytryptophan | L |

| Phenylglycine Family | |
|---|---|
| Compound | Isomer |
| phenylglycine | L |
| 4-hydroxyphenylglycine | L |
| 4-fluorophenylglycine | L |
| 4-methoxyphenylglycine | DL |
| amino-(4-nitro-phenyl)-acetic acid | DL |
| 4-trifluoromethylphenylglycine | L |
| 3-hydroxyphenylglycine | L |
| amino-(3-fluoro-phenyl)-acetic acid | DL |
| amino-(3-bromo-phenyl)-acetic acid | DL |
| 3-trifluoromethylphenylglycine | DL |
| amino-(3-nitro-phenyl)-acetic acid | DL |
| 2-fluorophenylglycine | DL |
| amino-o-tolyl-acetic acid | L |
| 2-chlorophenylglycine | DL |
| 3,4-difluorophenylglycine | DL |
| 3-chloro-4-fluorophenylglycine | DL |
| 3-fluoro-4-methyl phenylglycine | DL |
| 4-fluoro-3-methyl phenylglycine | DL |
| 3-carboxy-4-hydroxyphenylglycine | L |
| 2-Cl, 5-OH phenylglycine | DL |
| 3,4-dihydroxyphenylglycine | DL |
| 3,5-dihydroxyphenylglycine | DL |
| 4-carboxy-3-hydroxyphenylglycine | DL |
| 2-phenylglycine methylester | L |
| (4-methoxyphenyl)(methylamino)acetic acid | DL |
| 2-hydroxyphenylglycine | DL |
| amino-(2,3-dihydrobenzo [1,4]dioxin-6-yl)acetic acid | DL |
| amino-benzo[1,3]dioxol-5-yl acetic acid | DL |
| 2-amino-2-[3-hydroxy-4-(hydroxymethyl)phenyl]acetic acid | DL |
| (4-fluorophenyl)-morpholin-4yl-acetic acid | DL |
| cyclopropylalanine | L |

| Phenylalanine Family | |
|---|---|
| Compound | Isomer |
| homophenylalanine | L |
| 2-amino-5-phenylpentanoic acid | L |
| 4-hydroxyphenylalanine | L |
| 3,4-dihydroxyphenylalanine | L |
| Quisqualic acid | L |

| Compound | Isomer |
|---|---|
| Cysteine Family | |
| cysteine | L |
| S-methyl-cysteine | L |
| S-ethyl-cysteine | L |
| S-phenyl-cysteine | L |
| S-benzyl-cysteine | L |
| S-(4-methylphenyl)-cysteine | L |
| penicillamine | L |
| homocysteine | L |
| Serine/Threonine Family | |
| serine | L |
| serine | D |
| threonine | L |
| threonine | D |
| threonine | L-allo |
| threonine | DL-allo |
| O-methylserine | DL |
| O-acetylserine | L |
| benzylserine | L |
| beta (2-thienyl)serine | DL |
| 3-pyridylserine | DL |
| serine methylester | L |
| serine-beta-naphthylamide | L |
| methionine | L |
| 4-hydroxy-isoleucine | L |
| homoserine | D |
| homoserine | L |

| Cyclic Amino Acid Family | |
|---|---|
| Compound | Isomer |
| 1-amino-1-carboxycyclopropane | |
| 1-amino-1-carboxycyclobutane | |
| 1-amino-1-carboxycyclopentane | |
| homocysteine thiolactone | L |
| homoserine lactone | L |

| Proline Family | |
|---|---|
| Compound | Isomer |
| proline | L |
| 3,4-dehydroproline | L |
| 4-hydroxy-L-proline | trans |
| 4-fluoro-L-proline | trans |
| 4-fluoro-L-proline | cis |
| γ-benzyl-L-proline | R |
| γ-(4-fluorobenzyl)-L-proline | R |
| 1,2,3,4-tetrahydro-3-isoquinolinecarboxylic acid | S |
| 2,3,4,9-tetrahydro-1H-beta-carboline-3-carboxylic acid | DL |
| 2,3-dihydro-1H-isoindole-1-carboxylic acid | DL |

| Proline Family | |
|---|---|
| Compound | Isomer |
| 4H-thieno[3,2-b]pyrrole-5-carboxylic acid | |
| azetidine-2-carboxylic acid | L |
| proline-beta naphthylamide | L |
| trans-4-cyclohexylproline | L |
| trans-4-hydroxyproline-naphthylamide | L |
| 4,6-Dichloro-3-[(1E)-3-oxo-3-(phenylamino)-1-propenyl]-1H-indole-2-carboxylic acid | |
| (2S,3S,4S)-Carboxy-4-(1-methylethenyl)-3-pyrrolidineacetic acid 4-methoxy-7-nitro-1H-indolinyl amide | |
| (E)-4,6-Dichloro-3-(2-phenyl-2-carboxyethenyl)indole-2-carboxylic acid | |
| γ-allyl-L-proline | R |
| aziridine-2-carboxylic acid | L |
| γ-(4-nitrobenzyl)-L-proline | R |
| trans-4-phenylproline | L |
| γ-(3,4-difluorobenzyl)-L-proline | R |
| γ-(3-thienylmethyl)-L-proline | R |
| γ-(4-methylbenzyl)-L-proline | R |
| γ-(2-naphthylenylmethyl)-L-proline | R |
| γ-propynyl-L-proline | R |
| γ-(3-fluorobenzyl)-L-proline | R |
| γ-(2-fluorobenzyl)-L-proline | R |
| γ-(4-bromobenzyl)-L-proline | R |
| γ-(4-chlorobenzyl)-L-proline HCl | R |
| γ-(4-iodobenzyl)-L-proline HCl | R |
| 4H-thieno[3,2-b]pyrrole-5-carboxylic acid | |
| γ-(2-trifluromethylbenzyl)-L-proline HCl | R |
| γ-(4-tertbutylbenzyl)-L-proline HCl | R |
| 3-phenylproline | |
| γ-(2-cyanobenzyl)-L-proline HCl | R |
| γ-(2-methylbenzyl)-L-proline HCl | R |
| γ-(3-trifluoromethyl-benzyl)-L-proline HCl | R |
| γ-(3-phenyl-allyl)-L-proline HCl (Boc?) | R |
| γ-(1-naphthalenylmethyl)-L-proline HCl | R |
| 4-(3-chlorobenzyl)pyrrolidine-2-carboxylic acid HCl | 2S,4S |
| 4-(3-chlorobenzyl)pyrrolidine-2-carboxylic acid HCl | 2S,4R |
| 4-benzyl-L-proline | S |
| γ-(2-furanylmethyl)-L-proline | S |
| γ-(3-chlorobenzyl)-L-proline HCl | R |
| γ-(2-pyridinylmethyl)-L-proline 2HCl | S |
| 4-(3-chlorophenoxy)pyrrolidine-2-carboxylic acid HCl | 2S,4R |
| 4-(3-chlorophenoxy)pyrrolidine-2-carboxylic acid HCl | 2S,4S |
| γ-(2-iodobenzyl)-L-proline HCl | R |
| γ-(3-benzothienylmethyl)-L-proline HCl | R |
| γ-(2-bromobenzyl)-L-proline HCl | R |
| γ-(4-trifluoromethylbenzyl)-L-proline HCl | R |
| γ-(3-bromobenzyl)-L-proline HCl | R |
| γ-(4-pyridinylmethyl)-L-proline HCl | R |
| γ-(4-cyanobenzyl)-L-proline HCl | R |
| γ-(3-cyanobenzyl)-L-proline HCl | R |
| γ-(3,4-dichlorobenzyl)-L-proline HCl | R |
| γ-(2-chlorobenzyl)-L-proline HCl | R |
| γ-(2,4-dichlorobenzyl)-L-proline HCl | R |
| γ-propynyl-L-proline HCl | R |
| γ-(2-cyanobenzyl)-L-proline HCl | R |
| 3-methyl-2-pyrrolidine-2-carboxylic acid | 2S,3S |
| 3-phenyl-2-pyrrolidine-2-carboxylic acid | 2S,3R |
| (E)-4,6-Dichloro-3-(2-phenyl-2-carboxyethenyl)indole-2-carboxylic acid | |
| 4,6-Dichloro-3-[(1E)-3-oxo-3-(phenylamino)-1-propenyl]-1H-indole-2-carboxylic acid | |
| Carboxy-4-(1-methylethenyl)-3-pyrrolidineacetic acid 4-methoxy-7-nitro-1H-indolinyl amide | (2S,3S,4S) |

The compounds identified here in assays of D-serine transport are inhibitors of the transporter sub-types ASCT1 (SLC1A4) and ASCT2 (SLC1A5), as confirmed is transport assays using HEK cells that heterologously express human ASCT1 or ASCT2. This includes the compounds L-gamma-glutamyl-4-nitroanilide, L-4-hydroxyphenylglycine, L-4-fluorophenylglycine, L-phenylglycine, trans-4-hydroxy-L-proline and R-gamma-2,4-dichlorobenzyl-L-proline. These compounds have $IC_{50}$ values less than 2 mM in one or both assays of transport in HEK cells expressing ASCT1 or ASCT2.

Figure 8:
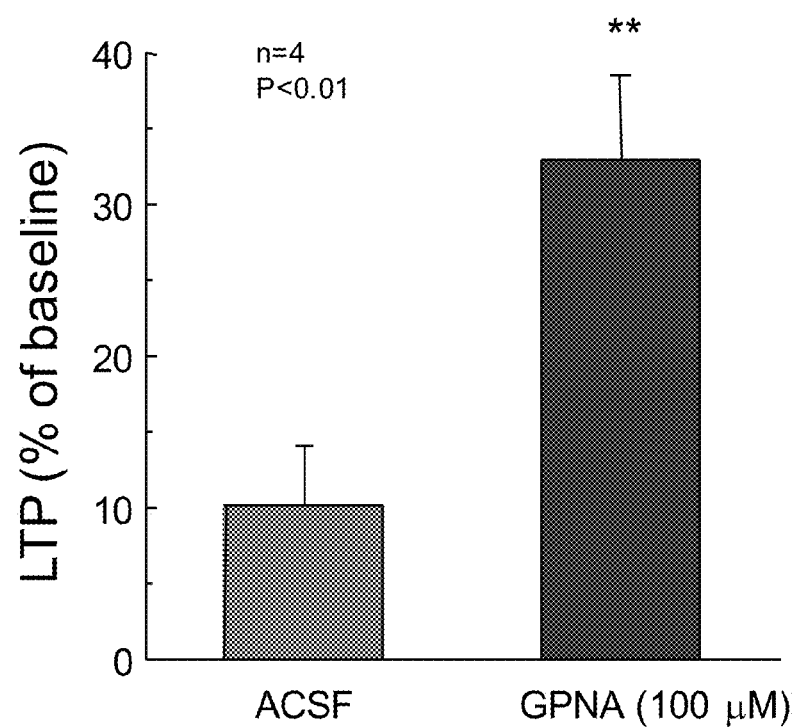
FIG. 8 represents a graph showing that 100 µM L-GPNA enhances LTP in the rat hippocampal slice preparation.

D-serine transport inhibitors may also have therapeutic benefits in central nervous system disorders where increasing NMDA receptor function is of benefit, including schizophrenia and Alzheimer's disease. For example, D-serine has been studied in several clinical trials of schizophrenic patients and has shown efficacy when added on to traditional antipsychotic drugs (Labrie and Roder, 2010). In the hippocampus, LTP is a synaptic strengthening that is believed to be an important mechanism in learning and memory (Citri and Malenka, 2007). The D-serine transport inhibitor L-GPNA was found to enhance LTP in the rat hippocampal slice (FIG. 8). This effect is likely due to a facilitation of NMDA-receptor mediated synaptic responses since, as shown earlier (FIG. 1), the D-serine transport inhibitor L-4OHPG was able to enhance NMDA-receptor-mediated epsc's in the rat hippocampal slice. These data indicate that D-serine transport inhibitors will be beneficial in enhancing cognitive abilities, for example in Alzheimer's disease patients.

The D-serine transport inhibitors were tested in a two well-established models of schizophrenia. Clinically-used antipsychotic drugs reduce amphetamine-induced hyperlocomotion and this assay has been widely used to profile antipsychotic drugs. Systemic administration of D-serine has been shown to reduce amphetamine-induced hyperlocomotion (Smith et al, 2009), a finding that corresponds with the efficacy of D-serine in schizophrenia clinical trials (Labrie and Roder, 2010). As shown in FIG. 9, systemic administration of L-4OHPG reduced amphetamine-induced hyperactivity in a dose-dependent manner. L-4FPG was a potent dose-dependent inhibitor of amphetamine-induced hyperlocomotion, with a significant effect at 0.3 mg/kg ip (FIG. 10). A compound from the proline family (R-gamma-(2,4,dichlorobenzyl)-L-proline) was also effective in this assay (FIG. 11). Paired-pulse inhibition (PPI) is a well-established model used to profile compounds for potential antipsychotic activity (Swerdlow and Geyer, 1998). D-serine and L-4OHPG were tested in a rat model of PPI. L-4OHPG reduced PPI, an effect that reached significance at the PP12 intensity level, and D-serine showed a similar trend that did not reach statistical significance (FIG. 12A). In a control experiment, neither L-4OHPG nor D-serine had any significant effect on the absolute startle response across the range of paired-pulse intensities used (FIG. 12B).

Taken together these data indicate that D-serine CNS transport inhibitors will be of benefit in the treatment of disorders such as schizophrenia and will improve cognition in conditions such as Alzheimer's disease.

General Procedures Followed in Obtaining Experimental Data

Electrophysiological Recording from Rat Hippocampal Slices (FIGS. 1A-1B):

350 µM thick hippocampal slices were prepared from 21- to 35-year-old rats using Leica VT1000S-microtome. Slices were perfused with ACSF containing: 121 mM NaCl, 2.5 mM KCl, 2.0 mM $Mg_2SO_4$, 2.0 $CaCl_2$, 1 mM $NaH_2PO_4$, 26.2 $NaHCO_3$, and 11 mM glucose, which was equilibrated with 5% $CO_2$/95% $O_2$. Experiments were performed in a recording chamber on the stage of an Olympus BX-61wi microscope with infrared DIC optics for visualizing whole-cell patch-clamp recordings. EPSPs were recorded from CA1 pyramidal neurons by stimulating the Schaffer collateral-commissural pathway using a bipolar tungsten electrode. The recording pipettes were filled with regular ICM containing: 120 mM Cs-gluconate, 5 mM NaCl, 10 mM KCl, 0.1 mM $CaCl_2$, 1 mM EGTA, 2 mM $MgCl_2$, 10 mM HEPES, 2 mM Na-ATP, 2 mM $Na_2$-phosphocreatine, and 0.25 mM Na-GTP, pH 7.3 (290 mOsm).

To measure NMDA-mediated EPSCs, extracellular $Mg_2SO_4$ was lowered to 0.2 mM and 2 µM NBQX and 100 µM picrotoxin were added in the ACSF. 1 µM 7-CKY (7-chlorokynurenic acid) was added to improve the sensitivity of $EPSC_{NMDA}$ to D-serine.

Figure 2A:
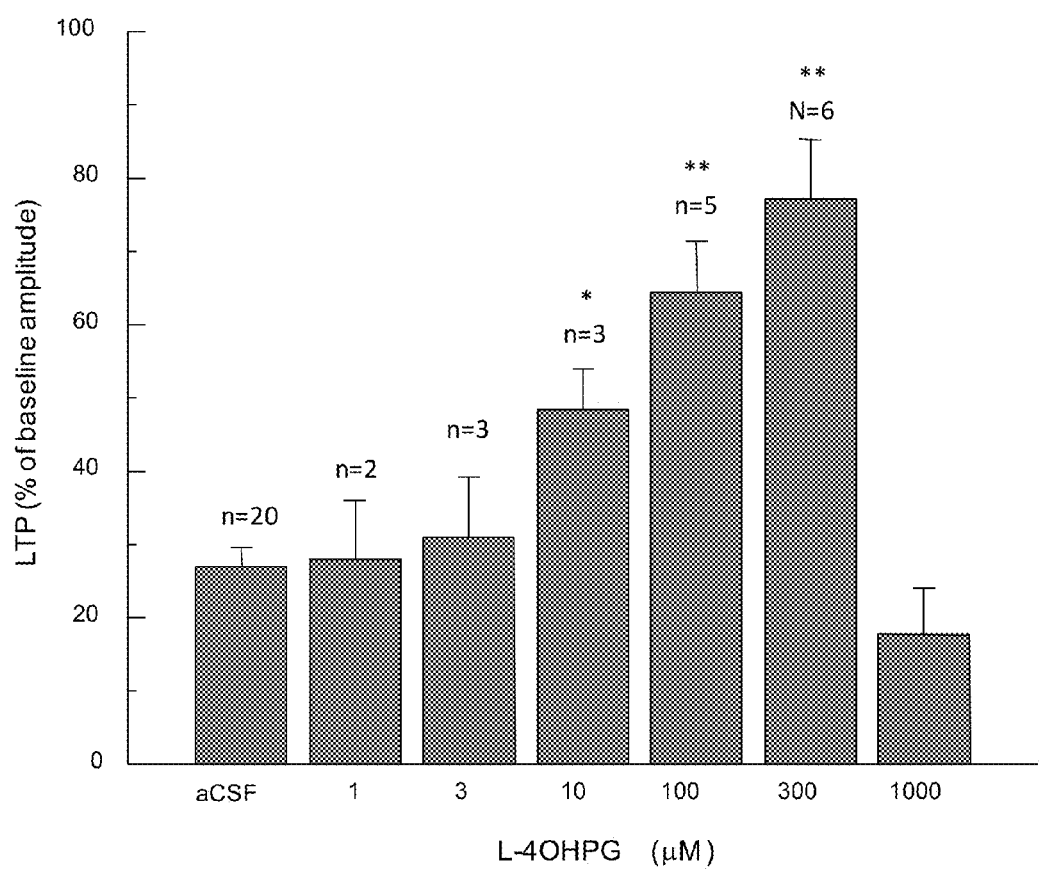
FIG. 2A represents a graph showing that L-4OHPG dose-dependently facilitates long-term potentiation (LTP) in the primary visual cortex of rats.
Figure 2B:
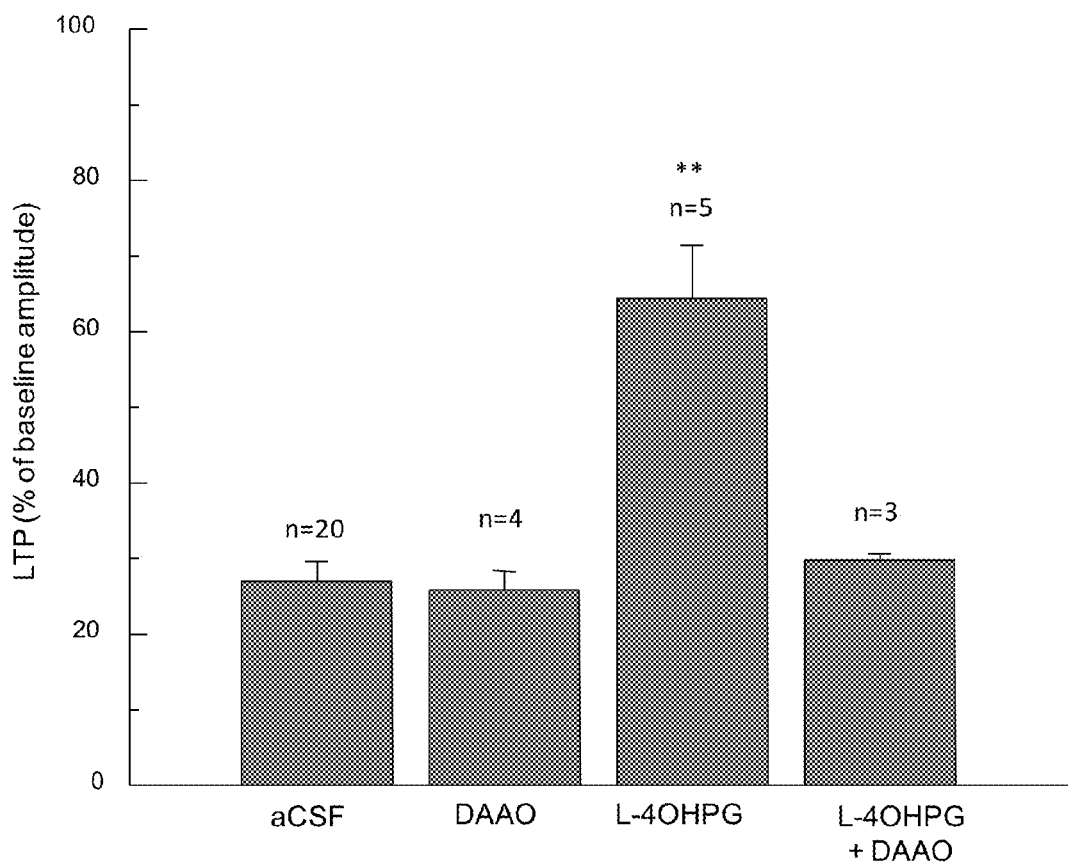
FIG. 2B represents a graph that features the results of exposing visual cortex slices to D-amino acid oxidase (DAAO), an enzyme that selectively degrades extracellular D-serine. The data suggest that L-4OHPG's enhancement of LTP in the visual cortex slice of rats is dependent on extracellular D-serine.

Long Term Potentiation in Primary Visual Cortex (FIG. 2)

Long Term Potentiation (LTP) in primary visual cortex has been used as a cellular model for visual cortex plasticity and has functional consequences on visual evoked responses. NMDA receptors play a critical role in visual cortex LTP induction.

Visual Cortex Slice Physiology:

Following decapitation of the rat, the brain was rapidly removed and immersed in ice-cold artificial cerebrospinal fluid (ACSF) containing 124 mM NaCl, 3 mM KCl, 1.25 mM $KH_2PO_4$, 3.4 mM $CaCl_2$, 2.5 mM $MgSO_4$, 26 mM $NaHCO_3$, and 10 mM D-glucose. A block of visual cortex was created by removing the frontal ⅔ portion of the brain and the cerebellum. Coronal visual cortex slices of 375 µm were prepared from adult Sprague Dawley (SD) rats using a vibratome (VT 1000 S; Leica). The slices were maintained in an interface recording chamber perfused with preheated ACSF. Slices were continuously perfused with this solution at a rate of 1.00-1.50 ml/min while the surface of the slices was exposed to warm, humidified 95% $O_2$/5% $CO_2$ and maintained at 31±1° C. Visual cortex slices were allowed to recover for 1 hr before recording began. A single stimulating and recording electrode were placed in layer IV and III, respectively, to generate and record a field excitatory postsynaptic potentials (fEPSPs). Pulses were administered every 20 s using a current that produced a fEPSP that was 50% of the maximum spike free response. An input-output (IO) curve was done to determine the stimulation needed to achieve a stable baseline. Following a 15 min stable baseline recording period, a train of 5 theta bursts (each burst containing four pulses at 100 Hz with an inter-burst interval of 200 ms) were delivered to the slice. This was repeated 2 additional times with a 1 minute intertrain interval, and the level of LTP was recorded for at least 30 min. Changes in amplitude of the synaptic response were used to measure the extent of LTP because it was determined to be the more consistent parameter than the slope of the response. Control LTP values were obtained from slices not treated with drug. Different slices were used to study drug effects on LTP. After a 15 min baseline recording period, the compounds of interest were infused for 15 minutes followed by LTP induction. Washout of the compounds began 5 minutes after tetanization. Recording of the amplitude before, during, and after drug infusion was done.

*DAAO Assay (FIG. 2B):

For experiments with DAAO, 0.2 unit/ml of DAAO were infused with or without the compounds of interest for 15 minutes before LTP induction.

Transport Experiments (Tables 1 and 2; FIGS. 4-6)

Cell-based assays: the transport of [$^3$H]L- or D-serine was measured in primary cultures of rat hippocampal astrocytes or in human embryonic kidney (HEK) cells expressing ASCT transporter sub-types. For the astrocyte assays, cells were plated on either 24- or 96-well plates at a density of 50,000 cells per well. For the HEK assays, cells were plated on coated 96-well plates at a density of 80,000 cells/well. Assays were conducted in duplicate at room temperature in assay buffer consisting of: NaCl: 150 mM, KCl: 2 mM; $MgCl_2$: 1 mM; $CaCl_2$: 1 mM; HEPES: Tris buffer: 10 mM, pH7.4. To assess the sodium-dependence of transport, NaCl was replaced in the assay buffer by equimolar choline chloride. Following aspiration of growth medium and 2 washes with assay buffer, cells were incubated with [$^3$H]L- or D-serine at a final concentration of 1 μM for 5 min (astrocytes) or 1 min (HEK cells), after which the incubation medium was aspirated and the cells washed twice with ice-cold assay buffer. Cells containing radiolabel were solubilized in 100 μl of 1% Triton-X100 and an aliquot counted in a beta counter. $IC_{50}$ values were determined over a range of at least 6 concentrations and derived from curve-fitting algorithms available in GraphPad Prism 4.

Synaptosome assays: a P2 fraction of rat forebrain was prepared and assayed immediately. Aliquots of the P2 preparation (approx. 1 mg of original tissue weight) were incubated in sodium-free assay buffer (CholineCl: 128 mM, KCl: 3.5 mM; $KH_2PO_4$: 1.5 mM; $MgCl_2$: 1 mM; $CaCl_2$: 1 mM; glucose: 10 mM; Tris-acetate buffer: 10 mM, pH7.4) containing [$^3$H]D-serine (final concentration of 50 nM) and test compounds in duplicate for 4 mins at room temperature. The synaptosomes containing radiolabel were collected by filtration onto Whatman GF/C filters, and washed twice with ice cold assay buffer. Filters were solubilized in scintillation fluid and radioactivity determined in a beta counter. $IC_{50}$ values were determined as described for the cell-based assays above.

Amphetamine Induced Hyperactivity (FIGS. 9, 10, 11)

C57B/6 male mice (n=5-10/group) were placed in an open field apparatus and their activity was measured for 30 minutes. At 30 minutes, they received a vehicle injection or injection of test compound followed by an injection of amphetamine (2 mg/kg, s.c.) at minute 45. Their activity levels were subsequently measured for another 1 hour post-injection. Total activity for each 5 minute bin (21 total bins) was added to establish the activity curve over the 105 minute testing.

Pre-Pulse Inhibition (FIGS. 12 A and B)

Pre-pulse inhibition was measured using the SR-Lab Startle Response system fitted with a rat enclosure. During the acclimation period, each rat (n=8/group) was habituated with a 5 min interval of 65-dB background noise followed by six 120 dB startle pulses alone, each 40 ms long. This acclimation phase was followed by a 15 min PPI test session where rats were presented with 120 dB startle pulses without a pre-pulse ("pulse alone") or pulses preceded by a 20 ms pre-pulse of 3, 6, or 12 dB above background noise ("PP3", "PP6", or "PP12", respectively) and ended with five 120 dB startle pulses. PPI was recorded for pre-pulse intensities of 3, 6, and 12 dB, and no stimulus. Each pre-pulse trial was administered in pseudorandom order. The 120 dB pulse alone trials were randomly interspersed within the pre-pulse trials and used for comparison with pre-pulse trials. PPI data were calculated as a percentage of PPI by comparing the pulse-alone versus the PP trials using the formula [100−(response to pre-pulse+120 dB)/(response to 120 dB alone)×100]. Experimenter was masked to treatment during testing and analysis.

Data were analyzed with a 2-way ANOVA with Condition and Treatment as factors with post hoc Bonferroni comparisons.

TABLE 1

| Compound | $IC_{50}$ in Astrocytes (μM) | $IC_{50}$ in Synaptosomes (μM) |
|---|---|---|
| L-serine | 57.9 | 9.6 |
| D-serine | 1581 | 9.4 |
| L-glutamine | 1641 | 943 |
| L-asparagine | 57.2 | 668 |
| L-GPNA | 3096 | 453 |
| L-glutamate-γ-benzyl ester | 3000 | 62 |
| L-4-fluorophenylglycine | 27.9 | 258 |
| L-4-hydroxyphenylglycine | 142.1 | 101 |
| DL-2-fluorophenylglycine | 1571 | 348 |
| L-phenylglycine | 89.4 | 217 |
| L-proline | 2271 | >10,000 |
| L-trans-4-hydroxyproline | 38.9 | >10,000 |
| S-benzyl-L-cysteine | 424 | 86 |
| S-phenyl-L-cysteine | 597 | 29.3 |

L-GPNA: L-γ-nitrophenyl glutamyl anilide.

We claim:

1. A method for the alleviation of a central nervous system disorder which is schizophrenia caused by a deficit in N-methyl-D-aspartate receptor function, the method comprising administering to a subject in need thereof an acceptable pharmaceutical composition containing a therapeutically effective amount of at least one ASCT1 inhibitor compound, which is L-4-fluoro phenylglycine and at least one ASCT2 inhibitor compound, which is L-4-fluoro phenylglycine.

2. A method for the alleviation of a central nervous system disorder which is schizophrenia caused by a deficit in N-methyl-D-aspartate receptor function, according to claim 1, the method comprising administering to a subject in need thereof an acceptable pharmaceutical composition containing a therapeutically effective amount of one ASCT1 inhibitor compound, which is L-4-fluoro phenylglycine.

3. A method for the alleviation of a central nervous system disorders caused by a deficit in N-methyl-D-aspartate receptor function, according to claim 1, the method comprising administering to a subject in need thereof an acceptable pharmaceutical composition containing a therapeutically effective amount of one ASCT2 inhibitor compound, which is L-4-fluoro phenylglycine.

* * * * *

UNITED STATES PATENT AND TRADEMARK OFFICE
CERTIFICATE OF CORRECTION

PATENT NO. : 8,741,955 B2
APPLICATION NO. : 13/480221
DATED : June 3, 2014
INVENTOR(S) : Alan C. Foster et al.

It is certified that error appears in the above-identified patent and that said Letters Patent is hereby corrected as shown below:

On the title page, item (56), under "Other Publications", in column 2, line 5, delete "andMechanisms"," and insert -- and Mechanisms", --, therefor.

On the title page, item (56), under "Other Publications", in column 2, line 15, delete "Chern" and insert -- Chem --, therefor.

On the title page, item (56), under "Other Publications", in column 2, line 25, delete "Physiol557.3:747-759," and insert -- Physiol 557.3:747-759, --, therefor.

On the title page 2, item (56), under "Other Publications", in column 1, line 16, delete "Chemestry," and insert -- Chemistry, --, therefor.

In the Drawings,

On sheet 3 of 18, FIG. 1B, line 1-2, after "Figure 1B", delete "Dose-response for L-4OHPG enhancement of NMDA Receptor-Mediated Excitatory Postsynaptic Currents (EPSC)".

On sheet 11 of 18, FIG. 6A, line 1-3, after "Figure 6A", delete "Transport of [$^3$H]D-serine by HEK cells expressing ASCT1 (SLC1A4) and ASCT2 (SLC1A5). The sodium-dependent transport of D-serine was similar in both cell lines.".

On sheet 13 of 18, FIG. 7, line 1-3, after "Figure 7", delete "Correlations between the ability of compounds to inhibit transport in HEK cells expressing ASCT1 and ASCT2 and the threshold concentration for LTP enhancement in the visual cortex".

On sheet 17 of 18, FIG. 11, line 1-2, after "Figure 11", delete "Effects of R-gamma (2,4 dichloro benzy)-L-proline (DCBPro) on amphetamine-induced hyperactivity in mice".

Signed and Sealed this
Eighteenth Day of November, 2014

Michelle K. Lee
*Deputy Director of the United States Patent and Trademark Office*

CERTIFICATE OF CORRECTION (continued)
U.S. Pat. No. 8,741,955 B2

In the Specification,

In column 3, line 31, delete "arylcyclohexyilamine" and insert -- arylcyclohexylamine --, therefor.

In column 3, line 34, delete "substancedementia," and insert -- substance dementia, --, therefor.

In column 5, line 34, delete "EPSC$_{NMDA}$" and insert -- EPSC$_{NMDA}$. --, therefor.

In column 14, line 54, delete "methyl phenylglycine" and insert -- methylphenylglycine --, therefor.

In column 14, line 55, delete "methyl phenylglycine" and insert -- methylphenylglycine --, therefor.

In column 16, line 28, delete "(2-trifluromethylbenzyl)" and insert -- (2-trifluoromethylbenzyl) --, therefor.

In column 16, line 44, delete "(4-trifuoromethylbenzyl)" and insert -- (4-trifluoromethylbenzyl) --, therefor.

In column 20, line 7-24, below "comparisons.", delete

TABLE 1

| Compound | IC$_{50}$ in Astrocytes (µM) | IC$_{50}$ in Synaptosomes (µM) |
|---|---|---|
| L-serine | 57.9 | 9.6 |
| D-serine | 1581 | 9.4 |
| L-glutamine | 1641 | 943 |
| L-asparagine | 57.2 | 668 |
| L-GPNA | 3096 | 453 |
| L-glutamate-γ-benzyl ester | 3000 | 62 |
| L-4-fluorophenylglycine | 27.9 | 258 |
| L-4-hydroxyphenylglycine | 142.1 | 101 |
| DL-2-fluorophenylglycine | 1571 | 348 |
| L-phenylglycine | 89.4 | 217 |
| L-proline | 2271 | >10,000 |
| L-trans-4-hydroxyproline | 38.9 | >10,000 |
| S-benzyl-L-cysteine | 424 | 86 |
| S-phenyl-L-cysteine | 597 | 29.3 |

" L-GPNA: L-γ-nitrophenyl glutamyl anilide.                 ".